United States Patent
Dorr et al.

(10) Patent No.: US 10,568,500 B2
(45) Date of Patent: Feb. 25, 2020

(54) METHODS AND SYSTEMS USING FRACTIONAL RANK PRECISION AND MEAN AVERAGE PRECISION AS TEST-RETEST RELIABILITY MEASURES

(71) Applicant: Adaptive Sensory Technology, Inc., San Diego, CA (US)

(72) Inventors: Michael Dorr, Munich (DE); Luis A. Lesmes, San Diego, CA (US)

(73) Assignee: Adaptive Sensory Technology, Inc., San Diego, CA (US)

( * ) Notice: Subject to any disclaimer, the term of this patent is extended or adjusted under 35 U.S.C. 154(b) by 58 days.

(21) Appl. No.: 15/965,614

(22) Filed: Apr. 27, 2018

(65) Prior Publication Data
US 2018/0242836 A1    Aug. 30, 2018

Related U.S. Application Data

(63) Continuation of application No. 15/146,632, filed on May 4, 2016, now Pat. No. 9,980,636.
(Continued)

(51) Int. Cl.
*A61B 3/00* (2006.01)
*A61B 3/14* (2006.01)
(Continued)

(52) U.S. Cl.
CPC ............ *A61B 3/0025* (2013.01); *A61B 3/022* (2013.01); *A61B 3/024* (2013.01); *A61B 3/063* (2013.01);
(Continued)

(58) Field of Classification Search
CPC ....... A61B 3/0025; A61B 3/022; A61B 3/024; A61B 3/063; A61B 3/1015; A61B 3/102;
(Continued)

(56) References Cited

U.S. PATENT DOCUMENTS

| | | |
|---|---|---|
| 7,856,332 B2 | 12/2010 | Karthikeyan et al. |
| 8,928,346 B2 | 1/2015 | Tenucci et al. |

(Continued)

FOREIGN PATENT DOCUMENTS

| | | | | |
|---|---|---|---|---|
| EP | 3292476 A1 | 3/2018 | | |
| WO | WO 2009/017483 | * | 2/2009 | ............... G06K 9/00 |

(Continued)

OTHER PUBLICATIONS

Chen et al; Repeatability and reproducibility of optic nerve head perfusion measurements using optical coherence tomography angiography. J. Biomed. Opt. 21(6):065002, 7 pages, 2016 doi:10.1117/1.JBO.21.6.065002.

(Continued)

*Primary Examiner* — Brandi N Thomas
(74) *Attorney, Agent, or Firm* — Wilson Sonsini Goodrich & Rosati

(57) ABSTRACT

Disclosed herein are methods and systems of evaluating test-retest precision using fractional rank precision or mean-average precision, comprising: a) collecting a test and a retest result of each subject, wherein the results are described in feature space(s) and collected from a vision test machine; b) selecting, a first test result of a first subject; c) calculating distances from the first test result to the retest result of each subject; d) assessing, a similarity between the first test result and the retest result of each subject by ranking the distances in a non-descending order; e) assessing a rank precision for the first subject based on a rank of a distance from the first test result to the retest result of the first subject; f) repeating b), c), d), and e) for each subject; and evaluating, the test-retest precision based on the rank precision for each of the plurality of subjects.

13 Claims, 8 Drawing Sheets

Related U.S. Application Data

(60) Provisional application No. 62/156,816, filed on May 4, 2015.

(51) Int. Cl.

| | | |
|---|---|---|
| *A61B 3/02* | (2006.01) | |
| *A61B 3/024* | (2006.01) | |
| *A61B 3/06* | (2006.01) | |
| *A61B 3/10* | (2006.01) | |
| *A61B 3/103* | (2006.01) | |
| *A61B 3/113* | (2006.01) | |
| *A61B 3/12* | (2006.01) | |
| *A61B 3/16* | (2006.01) | |
| *A61B 5/055* | (2006.01) | |
| *A61B 8/10* | (2006.01) | |
| *G06F 17/11* | (2006.01) | |

(52) U.S. Cl.
CPC .............. *A61B 3/102* (2013.01); *A61B 3/103* (2013.01); *A61B 3/1015* (2013.01); *A61B 3/113* (2013.01); *A61B 3/12* (2013.01); *A61B 3/14* (2013.01); *A61B 3/16* (2013.01); *A61B 5/055* (2013.01); *A61B 8/10* (2013.01); *G06F 17/11* (2013.01)

(58) Field of Classification Search
CPC ........... A61B 3/103; A61B 3/113; A61B 3/12; A61B 3/14; A61B 3/16; A61B 5/055; A61B 8/10
USPC ........ 351/200, 205–206, 209–211, 221–223, 351/243–245
See application file for complete search history.

(56) References Cited

U.S. PATENT DOCUMENTS

| | | |
|---|---|---|
| 9,980,636 B2 | 5/2018 | Dorr et al. |
| 2003/0125609 A1 | 7/2003 | Becker |
| 2007/0179398 A1 | 8/2007 | Margolis et al. |
| 2016/0353986 A1 | 12/2016 | Dorr et al. |

FOREIGN PATENT DOCUMENTS

| | | |
|---|---|---|
| WO | WO-2009017483 A1 | 2/2009 |
| WO | WO-2014158698 A1 | 10/2014 |
| WO | WO-2016179298 A1 | 11/2016 |

OTHER PUBLICATIONS

Dorr et. al., "Next-generation vision testing: the quick CSF." Current Directions in Biomedical Engineering, 1:131-134, 2015.

Dorr, et al., Average precision as a test-retest reliability measure: a quick CSF study on myopia. Poster. In ARVO 2015 Annual Meeting Abstracts, Program No. 3896, Poster Board No. D0038, 12 pages, 2015.

Guyatt et al., "Measuring change over time: Assessing the usefulness of evaluative instruments," Journal of Chronic Diseases, 40(2):171-178, 1987. [Online]. Available: http://www.sciencedirect.com/science/article/pii/0021968187900695.

J. M. Bland and D. G. Altman, "Statistical methods for assessing agreement between two methods of clinical measurement." Lancet, 1(8476):307-310, 1986.

Mueller et al., Comparison of a new image-guided system versus partial coherence interferometry, Scheimpflug imaging, and optical low-coherence reflectometry devices: Keratometry and repeatability. J Cataract Refract Surg., 42(5):672-678, 2016. doi: 10.1016/j.jcrs.2016.01.042.

Newman et al., Test-retest reliability of rapid whole body and compartmental fat volume quantification on a widebore 3T MR system in normal-weight, overweight, and obese subjects J Magn Reson Imaging 10 pages, 2016 doi: 10.1002/jmri.25326.

PCT Patent Application No. PCT/US2016/030810 International Search Report and Written Opinion dated Aug. 12, 2016.

PCT/US2016/030810 International Preliminary Report on Patentability dated Nov. 16, 2017.

Sabatino et al., Comparative analysis of optical biometers. J Cataract Refract Surg., 42(5):685- 693, 2016. doi: 10.1016/j.jcrs.2016.01.051.

Weber et al., Detailed quantitative assessment of colonic morphology at CT colonography using novel software: a feasibility and reproducibility study Med Biol Eng Comput., published online Jun. 11, 2016, 9 pages DOI 10.1007/s11517-016-1529-2.

Xu-Cheng Yin, et al., DeTEXT: A Database for Evaluating Text Extraction from Biomedical Literature Figures, PLoS One. 10(5): e0126200, 19 pages, 2015.

\* cited by examiner

METHODS AND SYSTEMS USING FRACTIONAL RANK PRECISION AND MEAN AVERAGE PRECISION AS TEST-RETEST RELIABILITY MEASURES

CROSS-REFERENCE TO RELATED APPLICATIONS

The present application is a continuation of U.S. application Ser. No. 15/146,632, entitled "METHODS AND SYSTEMS USING FRACTIONAL RANK PRECISION AND MEAN AVERAGE PRECISION AS TEST-RETEST RELIABILITY MEASURES" filed May 4, 2016, which claims the benefit of U.S. Provisional Application No. 62/156,816 filed May 4, 2015, the entire contents of which are incorporated herein by reference.

BACKGROUND

Clinically test-retest is typically used in monitoring of disease progression and/or effects of therapeutic treatment. Test-retest reliability is indicated by the variation in measurement results taken on a same subject in a test and in a subsequent retest. Such variability can be caused by a variety of factors including intra-individual variability and/or variability in measurement devices. A measurement may be considered as reliable when this variation is smaller than a pre-determined acceptance threshold.

SUMMARY OF THE INVENTION

Vision is one of the most important senses for many everyday tasks, and blindness ranks highly among most-feared ailments. Therefore, early diagnosis and treatment of vision loss are critical. As a result, regular monitoring of visual function at least in at-risk populations would be desirable. Certain vision tests rest on computationally intensive algorithms to provide a more comprehensive description of visual function. Thus, they have the potential to improve clinical care and research by more precise measurement of the effects of disease progression or ophthalmic interventions. A common proxy to study precision of a vision test is to assess its test-retest reliability; however, standard methods to assess clinical precision and test-retest reliability may be inadequate or even misleading for the more complex, higher-dimensional test outputs. Two major sources of imprecision typically are noise in the measurement device and moment-to-moment variability of the physiological phenomenon under observation. To estimate the contribution of noise in the device, precision is often assessed by the reliability of repeated measurements. The standard tools for this assessment are the intra-class correlation coefficient (ICC) and the Bland-Altman coefficient of repeatability (CoR). However, it is important to note that repeatability measures are an indirect assessment only; in the extreme case, a test with a binary outcome, as a non-limiting example, light perception, have almost perfect reliability but little discriminatory power for most of the population. Furthermore, the ICC is dominated by the values at either end of the test range and is therefore sensitive to outliers. The Bland-Altman coefficient of repeatability, which is defined as 1.96 times the standard deviation of differences between repeated measurements, does not suffer from this problem, and also may provide an intuitive threshold for how much change between two tests should be considered statistically significant. However, this threshold rests on the assumption that tests are homoscedastic, as a non-limiting example, the measurement error is independent of the magnitude of the ground truth (e.g. patients with poor vision perform tests as reliably as normal-sighted controls); its usefulness is limited by quantization of many tests, in addition to the evidence of heteroscedasticity in vision testing data. Moreover, absolute CoR values do not directly relate to clinical meaningfulness, and do not allow comparing the reliability of different tests with outputs of different magnitude or different dimensionality.

The methods and systems disclosed herein, in various embodiments, adapt at least one method in machine learning and/or information retrieval field and apply it in the measurement of similarity in test-retest pairs of at least one subject. In some embodiments, the methods and systems disclosed herein include at least a mean average precision method (MAP) adapted from machine learning and/or information retrieval. In some embodiments, the methods and systems disclosed herein include at least a fractional ranking precision (FRP) method derived from machine learning and/or information retrieval field. The methods and systems disclosed herein, for non-limiting examples, MAP and FRP, improve the limitations of traditional methods for the measurement of test-retest reliability and precision. Additionally, the methods and systems disclosed herein provide sensitivity (detection of subtle changes) and robustness (in the presence of artifacts) in evaluating the effectiveness of vision-based features in the detection of critical vision changes caused by disease progression and/or therapeutic interventions. Furthermore, the methods and systems disclosed herein enable assessment of vision-based features in multi-dimensional feature space.

In one aspect, disclosed herein are computer-implemented methods of evaluating test-retest precision of a test and a retest of a plurality of subjects using fractional rank precision (FRP) or mean-average precision (MAP), comprising: a) collecting, by a computer, a test result and a retest result of each of the plurality of subjects, wherein the test result and the retest result are described in one or more feature spaces and one of the test result and the retest result is collected from a vision test machine; b) selecting, by the computer, a first subject from the plurality of subjects and a first test result of the first subject; c) calculating, by the computer, distances from the first test result to the retest result of each of the plurality of subjects; d) assessing, by the computer, a similarity between the first test result and the retest result of each of the plurality of subjects by ranking the distances in a non-descending order; e) assessing, by the computer, a rank precision for the first subject based on a rank of a distance from the first test result to the retest result of the first subject; f) repeating, by the computer, steps b), c), d), and e) for each of the plurality of subjects; and g) evaluating, by the computer, the test-retest precision based on the rank precision for each of the plurality of subjects. In some embodiments, the test is a first vision test. In some embodiments, the retest is the first vision test or a second vision test. In some embodiments, the first vision test or the second vision test is one or more selected from: a vision acuity test, a CSF test, and an OCT test. In some embodiments, the feature space is one-dimensional or multi-dimensional. In some embodiments, the feature space comprises a feature. In some embodiments, the feature includes one or more features selected from: a median AULCSF computed over the spatial frequency range of 1.5 to 6 cpd, a median AULCSF computed over the spatial frequency range of 6 to 12 cpd, a median AULCSF computed over the spatial frequency range of 12 to 18 cpd, a median AULCSF computed over the spatial frequency range of 1.5 to 18 cpd, a CSF acuity, a parameter of CSF, a contrast sensitivity for at least one spatial frequency selected from 1, 1.5, 3, 6, 12, and 18 cpd, a peak sensitivity of the CSF, and a spatial frequency at which a CSF reaches a pre-determined contrast threshold. In some embodiments, the rank is a real number ranging from 0 to N−1, N being a total number of subjects in the plurality of subjects. In some embodiments, the rank is a real number ranging from 0 to N−1, N being a total number of retests of the plurality of subjects. In some embodiments, the distance is one or more selected from: a Euclidean distance, a Manhattan distance, and a Mahalanobis distance. In some embodiments, assessing the rank precision comprises: calculating a normalized rank, the normalized rank being the rank of the distance divided by a total number of subjects of the plurality of subjects; and calculating the rank precision, the rank precision being equal to one subtracted by the normalized rank. In some embodiments, the rank precision is an inverse of the rank of the retest result of the first subject. In some embodiments, the test-retest precision is mean of the rank precision for each of the plurality of subjects. In some embodiments, the test-retest precision is mean of the rank precision for each of the plurality of retest. In some embodiments, the rank is a real number ranging from 1 to N, N being a total number of subjects of the plurality of subjects. In some embodiments, he rank is a real number ranging from 1 to N, N being a total number of retests of the plurality of subjects. In some embodiments, the vision test machine is one or more selected from: a computerized adaptive contrast sensitivity testing device, a quick CSF (qCSF) testing device, a OCT machine, a MRI machine, an ultrasound machine, a visual field testing machine, a fundus photography system, a dark adaptation measurement machine, an auto-refractor machine, a frequency-doubling threshold machine, a tonometer machine, an aberrometer machine, an eye-tracking device, and an ocular alignment machine.

In another aspect, disclosed herein are computer-implemented systems comprising a digital processing device comprising at least one processor, an operating system configured to perform executable instructions, a memory, and a computer program including instructions executable by the digital processing device to create an application of evaluating test-retest precision of a test and a retest of a plurality of subjects using fractional rank precision (FRP) or mean-average precision (MAP), comprising: a) a software module configured to collect a test result and a retest result from each of the plurality of subjects, wherein the test result and the retest result are described in one or more feature spaces and one of the test result and the retest result is collected from a vision test machine; b) a software module configured to select a first subject from the plurality of subjects and a first test result of the first subject; c) a software module configured to calculate distances from the first test result to the retest result of each of the plurality of subjects; d) a software module configured to assess a similarity between the first test result and the retest result of each of the plurality of subjects by ranking the distances in a non-descending order; e) a software module configured to assess a rank precision for the first subject based on a rank of a distance from the first test result to the retest result of the first subject; f) a software module configured to repeat b), c), d), and e) for each of the plurality of subjects; and g) a software module configured to evaluate the test-retest precision based on the rank precision for each of the plurality of subjects. In some embodiments, the test is a first vision test. In some embodiments, the retest is the first vision test or a second vision test. In some embodiments, the first vision test or the second vision test is one or more selected from: a vision acuity test, a CSF test, and an OCT test. In some embodiments, the feature space is one-dimensional or multi-dimensional. In some embodiments, the feature space comprises a feature. In some embodiments, the feature includes one or more features selected from: a median AULCSF computed over the spatial frequency range of 1.5 to 6 cpd, a median AULCSF computed over the spatial frequency range of 6 to 12 cpd, a median AULCSF computed over the spatial frequency range of 12 to 18 cpd, a median AULCSF computed over the spatial frequency range of 1.5 to 18 cpd, a CSF acuity, a parameter of CSF, a contrast sensitivity for at least one spatial frequency selected from 1, 1.5, 3, 6, 12, and 18 cpd, a peak sensitivity of the CSF, and a spatial frequency at which a CSF reaches a pre-determined contrast threshold. In some embodiments, the rank is a real number ranging from 0 to N−1, N being a total number of subjects in the plurality of subjects. In some embodiments, the rank is a real number ranging from 0 to N−1, N being a total number of retests of the plurality of subjects. In some embodiments, the distance is one or more selected from: a Euclidean distance, a Manhattan distance, and a Mahalanobis distance. In some embodiments, assessing the rank precision comprises: calculating a normalized rank, the normalized rank being the rank of the distance divided by a total number of subjects of the plurality of subjects; and calculating the rank precision, the rank precision being equal to one subtracted by the normalized rank. In some embodiments, the rank precision is an inverse of the rank of the retest result of the first subject. In some embodiments, the test-retest precision is mean of the rank precision for each of the plurality of subjects. In some embodiments, the test-retest precision is mean of the rank precision for each of the plurality of retest. In some embodiments, the rank is a real number ranging from 1 to N, N being a total number of subjects of the plurality of subjects. In some embodiments, he rank is a real number ranging from 1 to N, N being a total number of retests of the plurality of subjects. In some embodiments, the vision test machine is one or more selected from: a computerized adaptive contrast sensitivity testing device, a qCSF testing device, a OCT machine, a MRI machine, an ultrasound machine, a visual field testing machine, a fundus photography system, a dark adaptation measurement machine, an auto-refractor machine, a frequency-doubling threshold machine, a tonometer machine, an aberrometer machine, an eye-tracking device, and an ocular alignment machine.

In another aspect, disclosed herein are non-transitory computer-readable storage media encoded with a computer program including instructions executable by a processor to create an application for evaluating test-retest precision of a test and a retest of a plurality of subjects using fractional rank precision (FRP) or mean-average precision (MAP), comprising: a) a database, in a computer memory, of a test result and a retest result for each of a plurality of subjects, wherein the test result and the retest result are described in one or more feature spaces, and one of the test result and the retest result is obtained from a vision test machine; b) a software module configured to select a first subject from the plurality of subjects and a first test result of the first subject; c) a software module configured to calculate distances from the first test result to the retest result of each of the plurality of subjects; d) a software module configured to assess a similarity between the first test result and the retest result of each of the plurality of subjects by ranking the distances in a non-descending order; e) a software module configured to assess a rank precision for the first subject based on a rank of a distance from the first test result to the retest result of the first subject; f) a software module configured to repeat b), c), d), and e) for each of the plurality of subjects; and g) a software module configured to evaluate the test-retest precision based on the rank precision for each of the plurality of subjects. In some embodiments, the test is a first vision test. In some embodiments, the retest is the first vision test or a second vision test. In some embodiments, the first vision test or the second vision test is one or more selected from: a vision acuity test, a CSF test, and an OCT test. In some embodiments, the feature space is one-dimensional or multi-dimensional. In some embodiments, the feature space comprises a feature. In some embodiments, the feature includes one or more features selected from: a median AULCSF computed over the spatial frequency range of 1.5 to 6 cpd, a median AULCSF computed over the spatial frequency range of 6 to 12 cpd, a median AULCSF computed over the spatial frequency range of 12 to 18 cpd, a median AULCSF computed over the spatial frequency range of 1.5 to 18 cpd, a CSF acuity, a parameter of CSF, a contrast sensitivity for at least one spatial frequency selected from 1, 1.5, 3, 6, 12, and 18 cpd, a peak sensitivity of the CSF, and a spatial frequency at which a CSF reaches a pre-determined contrast threshold. In some embodiments, the rank is a real number ranging from 0 to N−1, N being a total number of subjects in the plurality of subjects. In some embodiments, the rank is a real number ranging from 0 to N−1, N being a total number of retests of the plurality of subjects. In some embodiments, the distance is one or more selected from: a Euclidean distance, a Manhattan distance, and a Mahalanobis distance. In some embodiments, assessing the rank precision comprises: calculating a normalized rank, the normalized rank being the rank of the distance divided by a total number of subjects of the plurality of subjects; and calculating the rank precision, the rank precision being equal to one subtracted by the normalized rank. In some embodiments, the rank precision is an inverse of the rank of the retest result of the first subject. In some embodiments, the test-retest precision is mean of the rank precision for each of the plurality of subjects. In some embodiments, the test-retest precision is mean of the rank precision for each of the plurality of retest. In some embodiments, the rank is a real number ranging from 1 to N, N being a total number of subjects of the plurality of subjects. In some embodiments, he rank is a real number ranging from 1 to N, N being a total number of retests of the plurality of subjects. In some embodiments, the vision test machine is one or more selected from: a computerized adaptive contrast sensitivity testing device, a qCSF testing device, a OCT machine, a MRI machine, an ultrasound machine, a visual field testing machine, a fundus photography system, a dark adaptation measurement machine, an auto-refractor machine, a frequency-doubling threshold machine, a tonometer machine, an aberrometer machine, an eye-tracking device, and an ocular alignment machine.

In another aspect, disclosed herein are computer-implemented methods of evaluating test-retest precision of a test and a retest of a plurality of subjects using fractional rank precision (FRP) or mean-average precision (MAP), comprising: a) collecting, by a computer, a test result and a plurality of retest results from each of the plurality of subjects, wherein the test result and the plurality of retest results are described in one or more feature spaces, and one of the test result and the plurality of retest results is collected from a vision test machine; b) selecting, by the computer, a first subject from the plurality of subjects and a first test result of the first subject; c) calculating, by the computer, distances from the first test result to each of the plurality of retest results of each of the plurality of subjects; d) assessing, by the computer, a similarity between the first test result and the plurality of retest results of each of the plurality of subjects by ranking the distances in a non-descending order; e) assessing, by the computer, a rank precision for the first subject based on the rank of distances from the first test result to each of the plurality of retest results of the first subject; f) repeating, by the computer, steps b), c), d), and e) for each of the plurality of subjects; and g) evaluating, by the computer, the test-retest precision based on the rank precision for each of the plurality of subjects. In some embodiments, the test is a first vision test. In some embodiments, the retest is the first vision test or a second vision test. In some embodiments, the first vision test or the second vision test is one or more selected from: a vision acuity test, a CSF test, and an OCT test. In some embodiments, the feature space is one-dimensional or multi-dimensional. In some embodiments, the feature space comprises a feature. In some embodiments, the feature includes one or more features selected from: a median AULCSF computed over the spatial frequency range of 1.5 to 6 cpd, a median AULCSF computed over the spatial frequency range of 6 to 12 cpd, a median AULCSF computed over the spatial frequency range of 12 to 18 cpd, a median AULCSF computed over the spatial frequency range of 1.5 to 18 cpd, a CSF acuity, a parameter of CSF, a contrast sensitivity for at least one spatial frequency selected from 1, 1.5, 3, 6, 12, and 18 cpd, a peak sensitivity of the CSF, and a spatial frequency at which a CSF reaches a pre-determined contrast threshold. In some embodiments, the rank is a real number ranging from 0 to N−1, N being a total number of subjects in the plurality of subjects. In some embodiments, the rank is a real number ranging from 0 to N−1, N being a total number of retests of the plurality of subjects. In some embodiments, the distance is one or more selected from: a Euclidean distance, a Manhattan distance, and a Mahalanobis distance. In some embodiments, assessing the rank precision comprises: calculating a normalized rank, the normalized rank being the rank of the distance divided by a total number of subjects of the plurality of subjects; and calculating the rank precision, the rank precision being equal to one subtracted by the normalized rank. In some embodiments, the rank precision is an inverse of the rank of the retest result of the first subject. In some embodiments, the test-retest precision is mean of the rank precision for each of the plurality of subjects. In some embodiments, the test-retest precision is mean of the rank precision for each of the plurality of retest. In some embodiments, the rank is a real number ranging from 1 to N, N being a total number of subjects of the plurality of subjects. In some embodiments, he rank is a real number ranging from 1 to N, N being a total number of retests of the plurality of subjects. In some embodiments, the vision test machine is one or more selected from: a computerized adaptive contrast sensitivity testing device, a qCSF testing device, a OCT machine, a MRI machine, an ultrasound machine, a visual field testing machine, a fundus photography system, a dark adaptation measurement machine, an auto-refractor machine, a frequency-doubling threshold machine, a tonometer machine, an aberrometer machine, an eye-tracking device, and an ocular alignment machine.

In another aspect, disclosed herein are computer-implemented systems comprising a digital processing device comprising at least one processor, an operating system configured to perform executable instructions, a memory, and a computer program including instructions executable by the digital processing device to create an application of evaluating test-retest precision of a test and a retest of a plurality of subjects using fractional rank precision (FRP) or mean-average precision (MAP), comprising: a) a software module configured to collect a test result and a plurality of retest results from each of the plurality of subjects, wherein the test result and the plurality of retest results are described in one or more feature spaces, and one of the test result and the plurality of retest results is collected from a vision test machine; b) a software module configured to select a first subject from the plurality of subjects and a first test result of the first subject; c) a software module configured to calculate distances from the first test result to each of the plurality of retest results of each of the plurality of subjects; d) a software module configured to assess a similarity between the first test result and the plurality of retest results of each of the plurality of subjects by ranking the distances in a non-descending order; e) a software module configured to assess a rank precision for the first subject based on the rank of distances from the first test result to each of the plurality of retest results of the first subject; f) a software module configured to repeat b), c), d), and e) for each of the plurality of subjects; and g) a software module configured to evaluate the test-retest precision based on the rank precision for each of the plurality of subjects. In some embodiments, the test is a first vision test. In some embodiments, the retest is the first vision test or a second vision test. In some embodiments, the first vision test or the second vision test is one or more selected from: a vision acuity test, a CSF test, and an OCT test. In some embodiments, the feature space is one-dimensional or multi-dimensional. In some embodiments, the feature space comprises a feature. In some embodiments, the feature includes one or more features selected from: a median AULCSF computed over the spatial frequency range of 1.5 to 6 cpd, a median AULCSF computed over the spatial frequency range of 6 to 12 cpd, a median AULCSF computed over the spatial frequency range of 12 to 18 cpd, a median AULCSF computed over the spatial frequency range of 1.5 to 18 cpd, a CSF acuity, a parameter of CSF, a contrast sensitivity for at least one spatial frequency selected from 1, 1.5, 3, 6, 12, and 18 cpd, a peak sensitivity of the CSF, and a spatial frequency at which a CSF reaches a pre-determined contrast threshold. In some embodiments, the rank is a real number ranging from 0 to N−1, N being a total number of subjects in the plurality of subjects. In some embodiments, the rank is a real number ranging from 0 to N−1, N being a total number of retests of the plurality of subjects. In some embodiments, the distance is one or more selected from: a Euclidean distance, a Manhattan distance, and a Mahalanobis distance. In some embodiments, assessing the rank precision comprises: calculating a normalized rank, the normalized rank being the rank of the distance divided by a total number of subjects of the plurality of subjects; and calculating the rank precision, the rank precision being equal to one subtracted by the normalized rank. In some embodiments, the rank precision is an inverse of the rank of the retest result of the first subject. In some embodiments, the test-retest precision is mean of the rank precision for each of the plurality of subjects. In some embodiments, the test-retest precision is mean of the rank precision for each of the plurality of retest. In some embodiments, the rank is a real number ranging from 1 to N, N being a total number of subjects of the plurality of subjects. In some embodiments, he rank is a real number ranging from 1 to N, N being a total number of retests of the plurality of subjects. In some embodiments, the vision test machine is one or more selected from: a computerized adaptive contrast sensitivity testing device, a qCSF testing device, a OCT machine, a MRI machine, an ultrasound machine, a visual field testing machine, a fundus photography system, a dark adaptation measurement machine, an auto-refractor machine, a frequency-doubling threshold machine, a tonometer machine, an aberrometer machine, an eye-tracking device, and an ocular alignment machine.

In yet another aspect, disclosed herein are non-transitory computer-readable storage media encoded with a computer program including instructions executable by a processor to create an application for evaluating test-retest precision of a test and a retest of a plurality of subjects using fractional rank precision (FRP) or mean-average precision (MAP), comprising: a) a database, in a computer memory, of a test result and a plurality of retest results from each of the plurality of subjects, wherein the test result and the plurality of retest results are described in one or more feature spaces, and one of the test result and the plurality of retest results is collected from a vision test machine; b) a software module configured to select a first subject from the plurality of subjects and a first test result of the first subject; c) a software module configured to calculate distances from the first test result to each of the plurality of retest results of each of the plurality of subjects; d) a software module configured to assess a similarity between the first test result and the plurality of retest results of each of the plurality of subjects by ranking the distances in a non-descending order; e) a software module configured to assess a rank precision for the first subject based on the rank of distances from the first test result to each of the plurality of retest results of the first subject; f) a software module configured to repeat b), c), d), and e) for each of the plurality of subjects; and g) a software module configured to evaluate the test-retest precision based on the rank precision for each of the plurality of subjects. In some embodiments, the test is a first vision test. In some embodiments, the retest is the first vision test or a second vision test. In some embodiments, the first vision test or the second vision test is one or more selected from: a vision acuity test, a CSF test, and an OCT test. In some embodiments, the feature space is one-dimensional or multi-dimensional. In some embodiments, the feature space comprises a feature. In some embodiments, the feature includes one or more features selected from: a median AULCSF computed over the spatial frequency range of 1.5 to 6 cpd, a median AULCSF computed over the spatial frequency range of 6 to 12 cpd, a median AULCSF computed over the spatial frequency range of 12 to 18 cpd, a median AULCSF computed over the spatial frequency range of 1.5 to 18 cpd, a CSF acuity, a parameter of CSF, a contrast sensitivity for at least one spatial frequency selected from 1, 1.5, 3, 6, 12, and 18 cpd, a peak sensitivity of the CSF, and a spatial frequency at which a CSF reaches a pre-determined contrast threshold. In some embodiments, the rank is a real number ranging from 0 to N−1, N being a total number of subjects in the plurality of subjects. In some embodiments, the rank is a real number ranging from 0 to N−1, N being a total number of retests of the plurality of subjects. In some embodiments, the distance is one or more selected from: a Euclidean distance, a Manhattan distance, and a Mahalanobis distance. In some embodiments, assessing the rank precision comprises: calculating a normalized rank, the normalized rank being the rank of the distance divided by a total number of subjects of the plurality of subjects; and calculating the rank precision, the rank precision being equal to one subtracted by the normalized rank. In some embodiments, the rank precision is an inverse of the rank of the retest result of the first subject. In some embodiments, the test-retest precision is mean of the rank precision for each of the plurality of subjects. In some embodiments, the test-retest precision is mean of the rank precision for each of the plurality of retest. In some embodiments, the rank is a real number ranging from 1 to N, N being a total number of subjects of the plurality of subjects. In some embodiments, he rank is a real number ranging from 1 to N, N being a total number of retests of the plurality of subjects. In some embodiments, the vision test machine is one or more selected from: a computerized adaptive contrast sensitivity testing device, a qCSF testing device, a OCT machine, a MRI machine, an ultrasound machine, a visual field testing machine, a fundus photography system, a dark adaptation measurement machine, an auto-refractor machine, a frequency-doubling threshold machine, a tonometer machine, an aberrometer machine, an eye-tracking device, and an ocular alignment machine.

In yet another aspect, disclose herein are computer-implemented methods of evaluating test-retest precision of a test and a retest of a plurality of subjects using fractional rank precision (FRP) or mean-average precision (MAP), comprising: a) collecting, by a computer, a test result and a retest result of each of the plurality of subjects, wherein the test result and the retest result are described in one or more feature spaces and one of the test result and the retest result is collected from a vision test machine; b) selecting, by the computer, a nth subject from the plurality of subjects and the test result of the nth subject; c) calculating, by the computer, distances from the test result of the nth subject to the retest result of each of the plurality of subjects; d) assessing, by the computer, a similarity between the test result of the nth subject and the retest result of each of the plurality of subjects by ranking the distances in a non-descending order; e) assessing, by the computer, a rank precision for the nth subject based on the rank of the distance from the test result of the nth subject to the retest result of the nth subject; f) repeating, by the computer, steps b), c), d), and e) for $1 \leq n \leq N$, N being a total number of subjects in the plurality of subjects; and g) evaluating, by the computer, the test-retest precision based on the rank precision for each of the plurality of subjects. In some embodiments, the test is a first vision test. In some embodiments, the retest is the first vision test or a second vision test. In some embodiments, the first vision test or the second vision test is one or more selected from: a vision acuity test, a CSF test, and an OCT test. In some embodiments, the feature space is one-dimensional or multi-dimensional. In some embodiments, the feature space comprises a feature. In some embodiments, the feature includes one or more features selected from: a median AULCSF computed over the spatial frequency range of 1.5 to 6 cpd, a median AULCSF computed over the spatial frequency range of 6 to 12 cpd, a median AULCSF computed over the spatial frequency range of 12 to 18 cpd, a median AULCSF computed over the spatial frequency range of 1.5 to 18 cpd, a CSF acuity, a parameter of CSF, a contrast sensitivity for at least one spatial frequency selected from 1, 1.5, 3, 6, 12, and 18 cpd, a peak sensitivity of the CSF, and a spatial frequency at which a CSF reaches a pre-determined contrast threshold. In some embodiments, the rank is a real number ranging from 0 to N−1, N being a total number of subjects in the plurality of subjects. In some embodiments, the rank is a real number ranging from 0 to N−1, N being a total number of retests of the plurality of subjects. In some embodiments, the distance is one or more selected from: a Euclidean distance, a Manhattan distance, and a Mahalanobis distance. In some embodiments, assessing the rank precision comprises: calculating a normalized rank, the normalized rank being the rank of the distance divided by a total number of subjects of the plurality of subjects; and calculating the rank precision, the rank precision being equal to one subtracted by the normalized rank. In some embodiments, the rank precision is an inverse of the rank of the retest result of the first subject. In some embodiments, the test-retest precision is mean of the rank precision for each of the plurality of subjects. In some embodiments, the test-retest precision is mean of the rank precision for each of the plurality of retest. In some embodiments, the rank is a real number ranging from 1 to N, N being a total number of subjects of the plurality of subjects. In some embodiments, he rank is a real number ranging from 1 to N, N being a total number of retests of the plurality of subjects. In some embodiments, the vision test machine is one or more selected from: a computerized adaptive contrast sensitivity testing device, a qCSF testing device, a OCT machine, a MRI machine, an ultrasound machine, a visual field testing machine, a fundus photography system, a dark adaptation measurement machine, an auto-refractor machine, a frequency-doubling threshold machine, a tonometer machine, an aberrometer machine, an eye-tracking device, and an ocular alignment machine.

In yet another aspect, disclosed herein are computer-implemented systems comprising a digital processing device comprising at least one processor, an operating system configured to perform executable instructions, a memory, and a computer program including instructions executable by the digital processing device to create an application of evaluating test-retest precision of a test and a retest of a plurality of subjects using fractional rank precision (FRP) or mean-average precision (MAP), comprising: a) a software module configured to collect a test result and a retest result from each of the plurality of subjects, wherein the test result and the retest result are described in one or more feature spaces and one of the test result and the retest result is collected from a vision test machine; b) a software module configured to select a nth subject from the plurality of subjects and a test result of the nth subject; c) a software module configured to calculate distances from the test result of the nth subject to the retest result of each of the plurality of subjects; d) a software module configured to assess a similarity between the test result of the nth subject and the retest result of each of the plurality of subjects by ranking the distances in a non-descending order; e) a software module configured to assess a rank precision for the nth subject based on a rank of a distance from the test result of the nth subject to the retest result of the nth subject; f) repeating, by the computer, steps b), c), d), and e) for $1 \leq n \leq N$, N being a total number of subjects in the plurality of subjects; and g) a software module configured to evaluate the test-retest precision based on the rank precision for each of the plurality of subjects. In some embodiments, the test is a first vision test. In some embodiments, the retest is the first vision test or a second vision test. In some embodiments, the first vision test or the second vision test is one or more selected from: a vision acuity test, a CSF test, and an OCT test. In some embodiments, the feature space is one-dimensional or multi-dimensional. In some embodiments, the feature space comprises a feature. In some embodiments, the feature includes one or more features selected from: a median AULCSF computed over the spatial frequency range of 1.5 to 6 cpd, a median AULCSF computed over the spatial frequency range of 6 to 12 cpd, a median AULCSF computed over the spatial frequency range of 12 to 18 cpd, a median AULCSF computed over the spatial frequency range of 1.5 to 18 cpd, a CSF acuity, a parameter of CSF, a contrast sensitivity for at least one spatial frequency selected from 1, 1.5, 3, 6, 12, and 18 cpd, a peak sensitivity of the CSF, and a spatial frequency at which a CSF reaches a pre-determined contrast threshold. In some embodiments, the rank is a real number ranging from 0 to N−1, N being a total number of subjects in the plurality of subjects. In some embodiments, the rank is a real number ranging from 0 to N−1, N being a total number of retests of the plurality of subjects. In some embodiments, the distance is one or more selected from: a Euclidean distance, a Manhattan distance, and a Mahalanobis distance. In some embodiments, assessing the rank precision comprises: calculating a normalized rank, the normalized rank being the rank of the distance divided by a total number of subjects of the plurality of subjects; and calculating the rank precision, the rank precision being equal to one subtracted by the normalized rank. In some embodiments, the rank precision is an inverse of the rank of the retest result of the first subject. In some embodiments, the test-retest precision is mean of the rank precision for each of the plurality of subjects. In some embodiments, the test-retest precision is mean of the rank precision for each of the plurality of retest. In some embodiments, the rank is a real number ranging from 1 to N, N being a total number of subjects of the plurality of subjects. In some embodiments, he rank is a real number ranging from 1 to N, N being a total number of retests of the plurality of subjects. In some embodiments, the vision test machine is one or more selected from: a computerized adaptive contrast sensitivity testing device, a qCSF testing device, a OCT machine, a MRI machine, an ultrasound machine, a visual field testing machine, a fundus photography system, a dark adaptation measurement machine, an auto-refractor machine, a frequency-doubling threshold machine, a tonometer machine, an aberrometer machine, an eye-tracking device, and an ocular alignment machine.

In yet another aspect, disclosed herein are computer-implemented methods of evaluating test-retest precision of a test and a retest of a plurality of subjects using fractional rank precision (FRP) or mean-average precision (MAP), comprising: a) collecting, by a computer, a test result and a plurality of retest results from each of the plurality of subjects, wherein the test result and the plurality of retest results are described in one or more feature spaces, and one of the test result and the plurality of retest results is collected from a vision test machine; b) selecting, by the computer, a nth subject from the plurality of subjects and a test result of the nth subject; c) calculating, by the computer, distances from the test result of the nth subject to each of the plurality of retest results of each of the plurality of subjects; d) assessing, by the computer, a similarity between the test result of the nth subject and the plurality of retest results of each of the plurality of subjects by ranking the distances in a non-descending order; e) assessing, by the computer, a rank precision for the first subject based on the rank of distances from the test result of the nth subject to each of the plurality of retest results of the first subject; f) repeating, by the computer, steps b), c), d), and e) for 1≤n≤N, N being a total number of subjects in the plurality of subjects; and g) evaluating, by the computer, the test-retest precision based on the rank precision for each of the plurality of subjects. In some embodiments, the test is a first vision test. In some embodiments, the retest is the first vision test or a second vision test. In some embodiments, the first vision test or the second vision test is one or more selected from: a vision acuity test, a CSF test, and an OCT test. In some embodiments, the feature space is one-dimensional or multi-dimensional. In some embodiments, the feature space comprises a feature. In some embodiments, the feature includes one or more features selected from: a median AULCSF computed over the spatial frequency range of 1.5 to 6 cpd, a median AULCSF computed over the spatial frequency range of 6 to 12 cpd, a median AULCSF computed over the spatial frequency range of 12 to 18 cpd, a median AULCSF computed over the spatial frequency range of 1.5 to 18 cpd, a CSF acuity, a parameter of CSF, a contrast sensitivity for at least one spatial frequency selected from 1, 1.5, 3, 6, 12, and 18 cpd, a peak sensitivity of the CSF, and a spatial frequency at which a CSF reaches a pre-determined contrast threshold. In some embodiments, the rank is a real number ranging from 0 to N−1, N being a total number of subjects in the plurality of subjects. In some embodiments, the rank is a real number ranging from 0 to N−1, N being a total number of retests of the plurality of subjects. In some embodiments, the distance is one or more selected from: a Euclidean distance, a Manhattan distance, and a Mahalanobis distance. In some embodiments, assessing the rank precision comprises: calculating a normalized rank, the normalized rank being the rank of the distance divided by a total number of subjects of the plurality of subjects; and calculating the rank precision, the rank precision being equal to one subtracted by the normalized rank. In some embodiments, the rank precision is an inverse of the rank of the retest result of the first subject. In some embodiments, the test-retest precision is mean of the rank precision for each of the plurality of subjects. In some embodiments, the test-retest precision is mean of the rank precision for each of the plurality of retest. In some embodiments, the rank is a real number ranging from 1 to N, N being a total number of subjects of the plurality of subjects. In some embodiments, he rank is a real number ranging from 1 to N, N being a total number of retests of the plurality of subjects. In some embodiments, the vision test machine is one or more selected from: a computerized adaptive contrast sensitivity testing device, a qCSF testing device, a OCT machine, a MRI machine, an ultrasound machine, a visual field testing machine, a fundus photography system, a dark adaptation measurement machine, an auto-refractor machine, a frequency-doubling threshold machine, a tonometer machine, an aberrometer machine, an eye-tracking device, and an ocular alignment machine.

In yet another aspect disclosed herein are computer-implemented systems comprising a digital processing device comprising at least one processor, an operating system configured to perform executable instructions, a memory, and a computer program including instructions executable by the digital processing device to create an application of evaluating test-retest precision of a test and a retest of a plurality of subjects using fractional rank precision (FRP) or mean-average precision (MAP), comprising: a) a software module configured to collect a test result and a retest result from each of the plurality of subjects, wherein the test result and the retest result are described in one or more feature spaces and one of the test result and the retest result is collected from a vision test machine; b) a software module configured to select a nth subject from the plurality of subjects and a test result of the nth subject; c) a software module configured to calculate distances from the test result of the nth subject to the retest result of each of the plurality of subjects; d) a software module configured to assess a similarity between the test result of the nth subject and the retest result of each of the plurality of subjects by ranking the distances in a non-descending order; e) a software module configured to assess a rank precision for the nth subject based on a rank of a distance from the test result of the nth subject to the retest result of the nth subject; f) repeating, by the computer, steps b), c), d), and e) for $1 \leq n \leq N$, N being a total number of subjects in the plurality of subjects; and g) a software module configured to evaluate the test-retest precision based on the rank precision for each of the plurality of subjects. In some embodiments, the test is a first vision test. In some embodiments, the retest is the first vision test or a second vision test. In some embodiments, the first vision test or the second vision test is one or more selected from: a vision acuity test, a CSF test, and an OCT test. In some embodiments, the feature space is one-dimensional or multi-dimensional. In some embodiments, the feature space comprises a feature. In some embodiments, the feature includes one or more features selected from: a median AULCSF computed over the spatial frequency range of 1.5 to 6 cpd, a median AULCSF computed over the spatial frequency range of 6 to 12 cpd, a median AULCSF computed over the spatial frequency range of 12 to 18 cpd, a median AULCSF computed over the spatial frequency range of 1.5 to 18 cpd, a CSF acuity, a parameter of CSF, a contrast sensitivity for at least one spatial frequency selected from 1, 1.5, 3, 6, 12, and 18 cpd, a peak sensitivity of the CSF, and a spatial frequency at which a CSF reaches a pre-determined contrast threshold. In some embodiments, the rank is a real number ranging from 0 to N−1, N being a total number of subjects in the plurality of subjects. In some embodiments, the rank is a real number ranging from 0 to N−1, N being a total number of retests of the plurality of subjects. In some embodiments, the distance is one or more selected from: a Euclidean distance, a Manhattan distance, and a Mahalanobis distance. In some embodiments, assessing the rank precision comprises: calculating a normalized rank, the normalized rank being the rank of the distance divided by a total number of subjects of the plurality of subjects; and calculating the rank precision, the rank precision being equal to one subtracted by the normalized rank. In some embodiments, the rank precision is an inverse of the rank of the retest result of the first subject. In some embodiments, the test-retest precision is mean of the rank precision for each of the plurality of subjects. In some embodiments, the test-retest precision is mean of the rank precision for each of the plurality of retest. In some embodiments, the rank is a real number ranging from 1 to N, N being a total number of subjects of the plurality of subjects. In some embodiments, he rank is a real number ranging from 1 to N, N being a total number of retests of the plurality of subjects. In some embodiments, the vision test machine is one or more selected from: a computerized adaptive contrast sensitivity testing device, a qCSF testing device, a OCT machine, a MRI machine, an ultrasound machine, a visual field testing machine, a fundus photography system, a dark adaptation measurement machine, an auto-refractor machine, a frequency-doubling threshold machine, a tonometer machine, an aberrometer machine, an eye-tracking device, and an ocular alignment machine.

In yet another aspect, disclosed herein are computer-implemented systems comprising a digital processing device comprising at least one processor, an operating system configured to perform executable instructions, a memory, and a computer program including instructions executable by the digital processing device to create an application of evaluating test-retest precision of a test and a retest of a plurality of subjects using fractional rank precision (FRP) or mean-average precision (MAP), comprising: a) a software module configured to collect a test result and a plurality of retest results from each of the plurality of subjects, wherein the test result and the plurality of retest results are described in one or more feature spaces, and one of the test result and the plurality of retest results is collected from a vision test machine; b) a software module configured to select a nth subject from the plurality of subjects and a test result of the nth subject; c) a software module configured to calculate distances from the test result of the nth subject to each of the plurality of retest results of each of the plurality of subjects; d) a software module configured to assess a similarity between the test result of the nth subject and the plurality of retest results of each of the plurality of subjects by ranking the distances in a non-descending order; e) a software module configured to assess a rank precision for the nth subject based on the rank of distances from the test result of the nth subject to each of the plurality of retest results of the nth subject; f) a software module configured to repeat b), c), d), and e) for $1 \leq n \leq N$, N being a total number of subjects in the plurality of subjects; and g) a software module configured to evaluate the test-retest precision based on the rank precision for each of the plurality of subjects. In some embodiments, the test is a first vision test. In some embodiments, the retest is the first vision test or a second vision test. In some embodiments, the first vision test or the second vision test is one or more selected from: a vision acuity test, a CSF test, and an OCT test. In some embodiments, the feature space is one-dimensional or multi-dimensional. In some embodiments, the feature space comprises a feature. In some embodiments, the feature includes one or more features selected from: a median AULCSF computed over the spatial frequency range of 1.5 to 6 cpd, a median AULCSF computed over the spatial frequency range of 6 to 12 cpd, a median AULCSF computed over the spatial frequency range of 12 to 18 cpd, a median AULCSF computed over the spatial frequency range of 1.5 to 18 cpd, a CSF acuity, a parameter of CSF, a contrast sensitivity for at least one spatial frequency selected from 1, 1.5, 3, 6, 12, and 18 cpd, a peak sensitivity of the CSF, and a spatial frequency at which a CSF reaches a pre-determined contrast threshold. In some embodiments, the rank is a real number ranging from 0 to N−1, N being a total number of subjects in the plurality of subjects. In some embodiments, the rank is a real number ranging from 0 to N−1, N being a total number of retests of the plurality of subjects. In some embodiments, the distance is one or more selected from: a Euclidean distance, a Manhattan distance, and a Mahalanobis distance. In some embodiments, assessing the rank precision comprises: calculating a normalized rank, the normalized rank being the rank of the distance divided by a total number of subjects of the plurality of subjects; and calculating the rank precision, the rank precision being equal to one subtracted by the normalized rank. In some embodiments, the rank precision is an inverse of the rank of the retest result of the first subject. In some embodiments, the test-retest precision is mean of the rank precision for each of the plurality of subjects. In some embodiments, the test-retest precision is mean of the rank precision for each of the plurality of retest. In some embodiments, the rank is a real number ranging from 1 to N, N being a total number of subjects of the plurality of subjects. In some embodiments, he rank is a real number ranging from 1 to N, N being a total number of retests of the plurality of subjects. In some embodiments, the vision test machine is one or more selected from: a computerized adaptive contrast sensitivity testing device, a qCSF testing device, a OCT machine, a MRI machine, an ultrasound machine, a visual field testing machine, a fundus photography system, a dark adaptation measurement machine, an auto-refractor machine, a frequency-doubling threshold machine, a tonometer machine, an aberrometer machine, an eye-tracking device, and an ocular alignment machine.

DETAILED DESCRIPTION OF THE INVENTION

Figure 1:
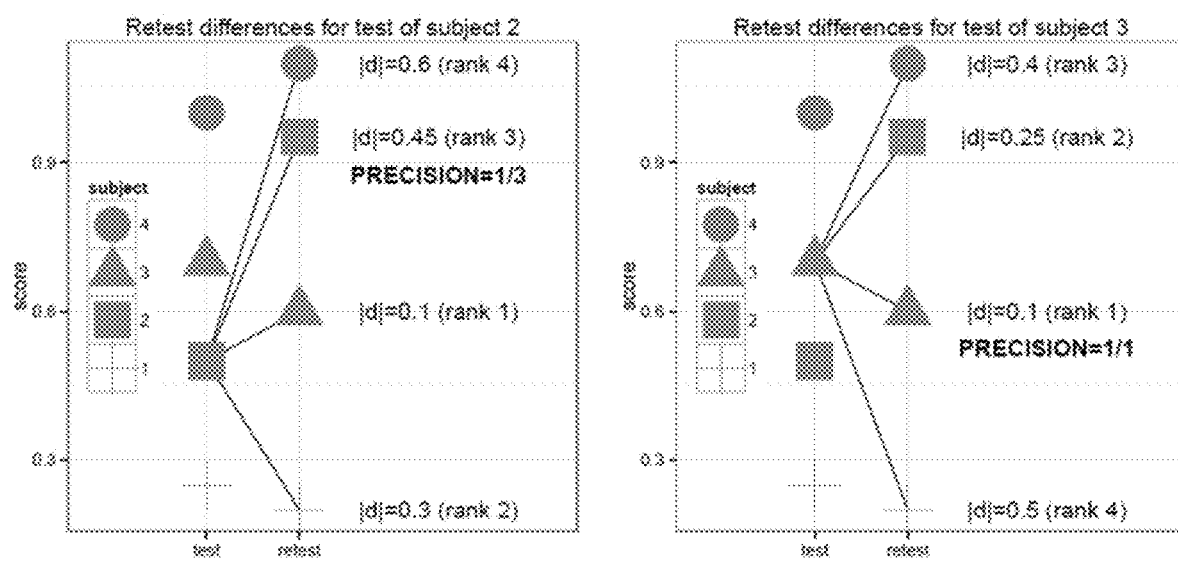
FIG. 1 shows a non-limiting example of the Mean Average Precision method disclosed herein; in this case, obtaining a distance and a rank of distance based on test-retest results of a subject.

The method and systems disclosed herein, in various embodiments, adapt at least one method in machine learning and/or information retrieval field and applies it in the measurement of similarity in test-retest pairs of at least one subject. In some embodiments, the methods and systems disclosed herein include at least a mean average precision method (MAP) adapted from machine learning and/or information retrieval. In some embodiments, the methods and systems disclosed herein include at least a fractional ranking precision (FRP) method derived from machine learning and/or information retrieval field. The methods and systems disclosed herein, for non-limiting examples, MAP and FRP, improve the limitations of traditional methods for the measurement of test-retest reliability and precision. Additionally, the methods and systems disclosed herein provide sensitivity (detection of subtle changes) and robustness (in the presence of artifacts) in evaluating the effectiveness of vision-based features in the detection of critical vision changes caused by disease progression and/or therapeutic interventions. Furthermore, the methods and systems disclosed herein enable assessment of vision-based features in multi-dimensional feature space.

In one aspect, disclosed herein are computer-implemented methods of evaluating test-retest precision of a test and a retest of a plurality of subjects using fractional rank precision (FRP) or mean-average precision (MAP), comprising: a) collecting, by a computer, a test result and a retest result of each of the plurality of subjects, wherein the test result and the retest result are described in one or more feature spaces and one of the test result and the retest result is collected from a vision test machine; b) selecting, by the computer, a first subject from the plurality of subjects and a first test result of the first subject; c) calculating, by the computer, distances from the first test result to the retest result of each of the plurality of subjects; d) assessing, by the computer, a similarity between the first test result and the retest result of each of the plurality of subjects by ranking the distances in a non-descending order; e) assessing, by the computer, a rank precision for the first subject based on a rank of a distance from the first test result to the retest result of the first subject; f) repeating, by the computer, steps b), c), d), and e) for each of the plurality of subjects; and g) evaluating, by the computer, the test-retest precision based on the rank precision for each of the plurality of subjects. In some embodiments, the test is a first vision test. In some embodiments, the retest is the first vision test or a second vision test. In some embodiments, the first vision test or the second vision test is one or more selected from: a vision acuity test, a CSF test, and an OCT test. In some embodiments, the feature space is one-dimensional or multi-dimensional. In some embodiments, the feature space comprises a feature. In some embodiments, the feature includes one or more features selected from: a median AULCSF computed over the spatial frequency range of 1.5 to 6 cpd, a median AULCSF computed over the spatial frequency range of 6 to 12 cpd, a median AULCSF computed over the spatial frequency range of 12 to 18 cpd, a median AULCSF computed over the spatial frequency range of 1.5 to 18 cpd, a CSF acuity, a parameter of CSF, a contrast sensitivity for at least one spatial frequency selected from 1, 1.5, 3, 6, 12, and 18 cpd, a peak sensitivity of the CSF, and a spatial frequency at which a CSF reaches a pre-determined contrast threshold. In some embodiments, the rank is a real number ranging from 0 to N−1, N being a total number of subjects in the plurality of subjects. In some embodiments, the rank is a real number ranging from 0 to N−1, N being a total number of retests of the plurality of subjects. In some embodiments, the distance is one or more selected from: a Euclidean distance, a Manhattan distance, and a Mahalanobis distance. In some embodiments, assessing the rank precision comprises: calculating a normalized rank, the normalized rank being the rank of the distance divided by a total number of subjects of the plurality of subjects; and calculating the rank precision, the rank precision being equal to one subtracted by the normalized rank. In some embodiments, the rank precision is an inverse of the rank of the retest result of the first subject. In some embodiments, the test-retest precision is mean of the rank precision for each of the plurality of subjects. In some embodiments, the test-retest precision is mean of the rank precision for each of the plurality of retest. In some embodiments, the rank is a real number ranging from 1 to N, N being a total number of subjects of the plurality of subjects. In some embodiments, he rank is a real number ranging from 1 to N, N being a total number of retests of the plurality of subjects. In some embodiments, the vision test machine is one or more selected from: a computerized adaptive contrast sensitivity testing device, a qCSF testing device, a OCT machine, a MRI machine, an ultrasound machine, a visual field testing machine, a fundus photography system, a dark adaptation measurement machine, an auto-refractor machine, a frequency-doubling threshold machine, a tonometer machine, an aberrometer machine, an eye-tracking device, and an ocular alignment machine.

In another aspect, disclosed herein are computer-implemented systems comprising a digital processing device comprising at least one processor, an operating system configured to perform executable instructions, a memory, and a computer program including instructions executable by the digital processing device to create an application of evaluating test-retest precision of a test and a retest of a plurality of subjects using fractional rank precision (FRP) or mean-average precision (MAP), comprising: a) a software module configured to collect a test result and a retest result from each of the plurality of subjects, wherein the test result and the retest result are described in one or more feature spaces and one of the test result and the retest result is collected from a vision test machine; b) a software module configured to select a first subject from the plurality of subjects and a first test result of the first subject; c) a software module configured to calculate distances from the first test result to the retest result of each of the plurality of subjects; d) a software module configured to assess a similarity between the first test result and the retest result of each of the plurality of subjects by ranking the distances in a non-descending order; e) a software module configured to assess a rank precision for the first subject based on a rank of a distance from the first test result to the retest result of the first subject; f) a software module configured to repeat b), c), d), and e) for each of the plurality of subjects; and g) a software module configured to evaluate the test-retest precision based on the rank precision for each of the plurality of subjects. In some embodiments, the test is a first vision test. In some embodiments, the retest is the first vision test or a second vision test. In some embodiments, the first vision test or the second vision test is one or more selected from: a vision acuity test, a CSF test, and an OCT test. In some embodiments, the feature space is one-dimensional or multi-dimensional. In some embodiments, the feature space comprises a feature. In some embodiments, the feature includes one or more features selected from: a median AULCSF computed over the spatial frequency range of 1.5 to 6 cpd, a median AULCSF computed over the spatial frequency range of 6 to 12 cpd, a median AULCSF computed over the spatial frequency range of 12 to 18 cpd, a median AULCSF computed over the spatial frequency range of 1.5 to 18 cpd, a CSF acuity, a parameter of CSF, a contrast sensitivity for at least one spatial frequency selected from 1, 1.5, 3, 6, 12, and 18 cpd, a peak sensitivity of the CSF, and a spatial frequency at which a CSF reaches a pre-determined contrast threshold. In some embodiments, the rank is a real number ranging from 0 to N−1, N being a total number of subjects in the plurality of subjects. In some embodiments, the rank is a real number ranging from 0 to N−1, N being a total number of retests of the plurality of subjects. In some embodiments, the distance is one or more selected from: a Euclidean distance, a Manhattan distance, and a Mahalanobis distance. In some embodiments, assessing the rank precision comprises: calculating a normalized rank, the normalized rank being the rank of the distance divided by a total number of subjects of the plurality of subjects; and calculating the rank precision, the rank precision being equal to one subtracted by the normalized rank. In some embodiments, the rank precision is an inverse of the rank of the retest result of the first subject. In some embodiments, the test-retest precision is mean of the rank precision for each of the plurality of subjects. In some embodiments, the test-retest precision is mean of the rank precision for each of the plurality of retest. In some embodiments, the rank is a real number ranging from 1 to N, N being a total number of subjects of the plurality of subjects. In some embodiments, he rank is a real number ranging from 1 to N, N being a total number of retests of the plurality of subjects. In some embodiments, the vision test machine is one or more selected from: a computerized adaptive contrast sensitivity testing device, a qCSF testing device, a OCT machine, a MRI machine, an ultrasound machine, a visual field testing machine, a fundus photography system, a dark adaptation measurement machine, an auto-refractor machine, a frequency-doubling threshold machine, a tonometer machine, an aberrometer machine, an eye-tracking device, and an ocular alignment machine.

In another aspect, disclosed herein are non-transitory computer-readable storage media encoded with a computer program including instructions executable by a processor to create an application for evaluating test-retest precision of a test and a retest of a plurality of subjects using fractional rank precision (FRP) or mean-average precision (MAP), comprising: a) a database, in a computer memory, of a test result and a retest result for each of a plurality of subjects, wherein the test result and the retest result are described in one or more feature spaces, and one of the test result and the retest result is obtained from a vision test machine; b) a software module configured to select a first subject from the plurality of subjects and a first test result of the first subject; c) a software module configured to calculate distances from the first test result to the retest result of each of the plurality of subjects; d) a software module configured to assess a similarity between the first test result and the retest result of each of the plurality of subjects by ranking the distances in a non-descending order; e) a software module configured to assess a rank precision for the first subject based on a rank of a distance from the first test result to the retest result of the first subject; f) a software module configured to repeat b), c), d), and e) for each of the plurality of subjects; and g) a software module configured to evaluate the test-retest precision based on the rank precision for each of the plurality of subjects. In some embodiments, the test is a first vision test. In some embodiments, the retest is the first vision test or a second vision test. In some embodiments, the first vision test or the second vision test is one or more selected from: a vision acuity test, a CSF test, and an OCT test. In some embodiments, the feature space is one-dimensional or multi-dimensional. In some embodiments, the feature space comprises a feature. In some embodiments, the feature includes one or more features selected from: a median AULCSF computed over the spatial frequency range of 1.5 to 6 cpd, a median AULCSF computed over the spatial frequency range of 6 to 12 cpd, a median AULCSF computed over the spatial frequency range of 12 to 18 cpd, a median AULCSF computed over the spatial frequency range of 1.5 to 18 cpd, a CSF acuity, a parameter of CSF, a contrast sensitivity for at least one spatial frequency selected from 1, 1.5, 3, 6, 12, and 18 cpd, a peak sensitivity of the CSF, and a spatial frequency at which a CSF reaches a pre-determined contrast threshold. In some embodiments, the rank is a real number ranging from 0 to N−1, N being a total number of subjects in the plurality of subjects. In some embodiments, the rank is a real number ranging from 0 to N−1, N being a total number of retests of the plurality of subjects. In some embodiments, the distance is one or more selected from: a Euclidean distance, a Manhattan distance, and a Mahalanobis distance. In some embodiments, assessing the rank precision comprises: calculating a normalized rank, the normalized rank being the rank of the distance divided by a total number of subjects of the plurality of subjects; and calculating the rank precision, the rank precision being equal to one subtracted by the normalized rank. In some embodiments, the rank precision is an inverse of the rank of the retest result of the first subject. In some embodiments, the test-retest precision is mean of the rank precision for each of the plurality of subjects. In some embodiments, the test-retest precision is mean of the rank precision for each of the plurality of retest. In some embodiments, the rank is a real number ranging from 1 to N, N being a total number of subjects of the plurality of subjects. In some embodiments, he rank is a real number ranging from 1 to N, N being a total number of retests of the plurality of subjects. In some embodiments, the vision test machine is one or more selected from: a computerized adaptive contrast sensitivity testing device, a qCSF testing device, a OCT machine, a MRI machine, an ultrasound machine, a visual field testing machine, a fundus photography system, a dark adaptation measurement machine, an auto-refractor machine, a frequency-doubling threshold machine, a tonometer machine, an aberrometer machine, an eye-tracking device, and an ocular alignment machine.

In another aspect, disclosed herein are computer-implemented methods of evaluating test-retest precision of a test and a retest of a plurality of subjects using fractional rank precision (FRP) or mean-average precision (MAP), comprising: a) collecting, by a computer, a test result and a plurality of retest results from each of the plurality of subjects, wherein the test result and the plurality of retest results are described in one or more feature spaces, and one of the test result and the plurality of retest results is collected from a vision test machine; b) selecting, by the computer, a first subject from the plurality of subjects and a first test result of the first subject; c) calculating, by the computer, distances from the first test result to each of the plurality of retest results of each of the plurality of subjects; d) assessing, by the computer, a similarity between the first test result and the plurality of retest results of each of the plurality of subjects by ranking the distances in a non-descending order; e) assessing, by the computer, a rank precision for the first subject based on the rank of distances from the first test result to each of the plurality of retest results of the first subject; f) repeating, by the computer, steps b), c), d), and e) for each of the plurality of subjects; and g) evaluating, by the computer, the test-retest precision based on the rank precision for each of the plurality of subjects.

In another aspect, disclosed herein are computer-implemented systems comprising a digital processing device comprising at least one processor, an operating system configured to perform executable instructions, a memory, and a computer program including instructions executable by the digital processing device to create an application of evaluating test-retest precision of a test and a retest of a plurality of subjects using fractional rank precision (FRP) or mean-average precision (MAP), comprising: a) a software module configured to collect a test result and a plurality of retest results from each of the plurality of subjects, wherein the test result and the plurality of retest results are described in one or more feature spaces, and one of the test result and the plurality of retest results is collected from a vision test machine; b) a software module configured to select a first subject from the plurality of subjects and a first test result of the first subject; c) a software module configured to calculate distances from the first test result to each of the plurality of retest results of each of the plurality of subjects; d) a software module configured to assess a similarity between the first test result and the plurality of retest results of each of the plurality of subjects by ranking the distances in a non-descending order; e) a software module configured to assess a rank precision for the first subject based on the rank of distances from the first test result to each of the plurality of retest results of the first subject; f) a software module configured to repeat b), c), d), and e) for each of the plurality of subjects; and g) a software module configured to evaluate the test-retest precision based on the rank precision for each of the plurality of subjects.

In yet another aspect, disclosed herein are non-transitory computer-readable storage media encoded with a computer program including instructions executable by a processor to create an application for evaluating test-retest precision of a test and a retest of a plurality of subjects using fractional rank precision (FRP) or mean-average precision (MAP), comprising: a) a database, in a computer memory, of a test result and a plurality of retest results from each of the plurality of subjects, wherein the test result and the plurality of retest results are described in one or more feature spaces, and one of the test result and the plurality of retest results is collected from a vision test machine; b) a software module configured to select a first subject from the plurality of subjects and a first test result of the first subject; c) a software module configured to calculate distances from the first test result to each of the plurality of retest results of each of the plurality of subjects; d) a software module configured to assess a similarity between the first test result and the plurality of retest results of each of the plurality of subjects by ranking the distances in a non-descending order; e) a software module configured to assess a rank precision for the first subject based on the rank of distances from the first test result to each of the plurality of retest results of the first subject; f) a software module configured to repeat b), c), d), and e) for each of the plurality of subjects; and g) a software module configured to evaluate the test-retest precision based on the rank precision for each of the plurality of subjects.

In yet another aspect, disclose herein are computer-implemented methods of evaluating test-retest precision of a test and a retest of a plurality of subjects using fractional rank precision (FRP) or mean-average precision (MAP), comprising: a) collecting, by a computer, a test result and a retest result of each of the plurality of subjects, wherein the test result and the retest result are described in one or more feature spaces and one of the test result and the retest result is collected from a vision test machine; b) selecting, by the computer, a nth subject from the plurality of subjects and the test result of the nth subject; c) calculating, by the computer, distances from the test result of the nth subject to the retest result of each of the plurality of subjects; d) assessing, by the computer, a similarity between the test result of the nth subject and the retest result of each of the plurality of subjects by ranking the distances in a non-descending order; e) assessing, by the computer, a rank precision for the nth subject based on the rank of the distance from the test result of the nth subject to the retest result of the nth subject; f) repeating, by the computer, steps b), c), d), and e) for $1 \leq n \leq N$, N being a total number of subjects in the plurality of subjects; and g) evaluating, by the computer, the test-retest precision based on the rank precision for each of the plurality of subjects.

In yet another aspect, disclosed herein are computer-implemented systems comprising a digital processing device comprising at least one processor, an operating system configured to perform executable instructions, a memory, and a computer program including instructions executable by the digital processing device to create an application of evaluating test-retest precision of a test and a retest of a plurality of subjects using fractional rank precision (FRP) or mean-average precision (MAP), comprising: a) a software module configured to collect a test result and a retest result from each of the plurality of subjects, wherein the test result and the retest result are described in one or more feature spaces and one of the test result and the retest result is collected from a vision test machine; b) a software module configured to select a nth subject from the plurality of subjects and a test result of the nth subject; c) a software module configured to calculate distances from the test result of the nth subject to the retest result of each of the plurality of subjects; d) a software module configured to assess a similarity between the test result of the nth subject and the retest result of each of the plurality of subjects by ranking the distances in a non-descending order; e) a software module configured to assess a rank precision for the nth subject based on a rank of a distance from the test result of the nth subject to the retest result of the nth subject; f) repeating, by the computer, steps b), c), d), and e) for 1≤n≤N, N being a total number of subjects in the plurality of subjects; and g) a software module configured to evaluate the test-retest precision based on the rank precision for each of the plurality of subjects.

In yet another aspect, disclosed herein are computer-implemented methods of evaluating test-retest precision of a test and a retest of a plurality of subjects using fractional rank precision (FRP) or mean-average precision (MAP), comprising: a) collecting, by a computer, a test result and a plurality of retest results from each of the plurality of subjects, wherein the test result and the plurality of retest results are described in one or more feature spaces, and one of the test result and the plurality of retest results is collected from a vision test machine; b) selecting, by the computer, a nth subject from the plurality of subjects and a test result of the nth subject; c) calculating, by the computer, distances from the test result of the nth subject to each of the plurality of retest results of each of the plurality of subjects; d) assessing, by the computer, a similarity between the test result of the nth subject and the plurality of retest results of each of the plurality of subjects by ranking the distances in a non-descending order; e) assessing, by the computer, a rank precision for the first subject based on the rank of distances from the test result of the nth subject to each of the plurality of retest results of the first subject; f) repeating, by the computer, steps b), c), d), and e) for 1≤n≤N, N being a total number of subjects in the plurality of subjects; and g) evaluating, by the computer, the test-retest precision based on the rank precision for each of the plurality of subjects.

In yet another aspect disclosed herein are computer-implemented systems comprising a digital processing device comprising at least one processor, an operating system configured to perform executable instructions, a memory, and a computer program including instructions executable by the digital processing device to create an application of evaluating test-retest precision of a test and a retest of a plurality of subjects using fractional rank precision (FRP) or mean-average precision (MAP), comprising: a) a software module configured to collect a test result and a retest result from each of the plurality of subjects, wherein the test result and the retest result are described in one or more feature spaces and one of the test result and the retest result is collected from a vision test machine; b) a software module configured to select a nth subject from the plurality of subjects and a test result of the nth subject; c) a software module configured to calculate distances from the test result of the nth subject to the retest result of each of the plurality of subjects; d) a software module configured to assess a similarity between the test result of the nth subject and the retest result of each of the plurality of subjects by ranking the distances in a non-descending order; e) a software module configured to assess a rank precision for the nth subject based on a rank of a distance from the test result of the nth subject to the retest result of the nth subject; f) repeating, by the computer, steps b), c), d), and e) for 1≤n≤N, N being a total number of subjects in the plurality of subjects; and g) a software module configured to evaluate the test-retest precision based on the rank precision for each of the plurality of subjects.

In yet another aspect, disclosed herein are computer-implemented systems comprising a digital processing device comprising at least one processor, an operating system configured to perform executable instructions, a memory, and a computer program including instructions executable by the digital processing device to create an application of evaluating test-retest precision of a test and a retest of a plurality of subjects using fractional rank precision (FRP) or mean-average precision (MAP), comprising: a) a software module configured to collect a test result and a plurality of retest results from each of the plurality of subjects, wherein the test result and the plurality of retest results are described in one or more feature spaces, and one of the test result and the plurality of retest results is collected from a vision test machine; b) a software module configured to select a nth subject from the plurality of subjects and a test result of the nth subject; c) a software module configured to calculate distances from the test result of the nth subject to each of the plurality of retest results of each of the plurality of subjects; d) a software module configured to assess a similarity between the test result of the nth subject and the plurality of retest results of each of the plurality of subjects by ranking the distances in a non-descending order; e) a software module configured to assess a rank precision for the nth subject based on the rank of distances from the test result of the nth subject to each of the plurality of retest results of the nth subject; f) a software module configured to repeat b), c), d), and e) for 1≤n≤N, N being a total number of subjects in the plurality of subjects; and g) a software module configured to evaluate the test-retest precision based on the rank precision for each of the plurality of subjects.

Overview

Human vision is one of the most important senses for many everyday tasks, and blindness ranks highly among most-feared ailments. Therefore, early diagnosis and treatment of vision loss are critical. As a result, regular monitoring of visual function at least in at-risk populations would be desirable. Certain vision tests rest on computationally intensive algorithms to provide a more comprehensive description of visual function. Thus, they have the potential to improve clinical care and research by more precise measurement of the effects of disease progression or ophthalmic interventions. A common proxy to study precision of a test is to assess its test-retest reliability; however, standard methods to assess clinical precision and test-retest reliability may be inadequate or even misleading for the more complex, higher-dimensional test outputs. Two major sources of imprecision typically are noise in the measurement device and moment-to-moment variability of the physiological phenomenon under observation. To estimate the contribution of noise in the device, precision is often assessed by the reliability of repeated measurements. The standard tools for this assessment are the intra-class correlation coefficient (ICC) and the Bland-Altman coefficient of repeatability (CoR). However, it is important to note that repeatability measures are an indirect assessment only; in the extreme case, a test with a binary outcome, as a non-limiting example, light perception, may have almost perfect reliability but little discriminatory power for most of the population. Furthermore, the ICC is dominated by the values at either end of the test range and is therefore sensitive to outliers.

The Bland-Altman coefficient of repeatability, which is defined as 1.96 times the standard deviation of differences between repeated measurements, does not suffer from this problem, and also may provide an intuitive threshold for how much change between two tests should be considered statistically significant. However, this threshold rests on the assumption that tests are homoscedastic, as a non-limiting example, the measurement error is independent of the magnitude of the ground truth (e.g. patients with poor vision perform tests as reliably as normal-sighted controls); its usefulness is limited by quantization of many tests, in addition to the evidence of heteroscedasticity in vision testing data. Moreover, absolute CoR values do not directly relate to clinical meaningfulness, and do not allow comparing the reliability of different tests with outputs of different magnitude or different dimensionality.

In some embodiments, the methods and systems disclosed herein relate to the information retrieval field. In some embodiments, the methods and systems disclosed herein use method(s) in information retrieval. The methods and systems disclosed herein, in various embodiments, are applied in order to evaluate similarity, repeatability, reliability, precision, or variability of a test-retest pair. In some embodiments, the methods and systems disclosed herein are used for multiple subjects with each subject having at least one test and at least one retest result. In some embodiments, method disclosed herein, for non-limiting examples, MAP and FRP, are particularly useful for test-retest results in higher-dimensional feature spaces including quick CSF (qCSF) results, traditional CSF measurements at different spatial frequencies, imaging modalities such as fundus photography or OCT, and perimetry results of different locations in the visual field. For traditional tests with scalar outcomes, it is relatively easy to statistically describe some aspects of test-retest variability, for example "95% of test-retest pairs will be less than X units apart." However, there are limitations with that method (as a non-limiting example, dependence on test range and quantization); such limitations get much worse in a multi-dimensional space, when test-retest differences are expressed as a multi-dimensional vector. However, MAP or FRP methods are suited for describing relationships or point distances within higher-dimensional feature spaces. In some embodiments, MAP and FRP methods can not only be applied to individual features or combinations of features of a specific vision test, but also be applied to combine results from different tests including one or more functional, behavior, or structural tests. Further, MAP or FRP methods can be used to compare and select individual features or different combination of features based on their test-retest precision performance. In some embodiments, CoR and ICC are more vulnerable to artifacts than MAP and FRP for measuring test-retest similarity. In some embodiments, MAP and FRP are more accurate in capturing a test's precision by expressing test-retest variability in terms of population variability. In some embodiments, MAP and FRP penalize coarse quantization in the test-retest results.

Tests and Retests

In some embodiments, the methods and systems disclosed herein include a test and a retest. In some embodiments, a test and a retest is examination of one or more visionary feature using specialized and suitable medical machine capable of measuring the feature(s). In some embodiments, a test and a retest is examination of one or more visionary features as disclosed herein. In some embodiments, a test and a retest is a procedure whose result is described by one or more visionary features as disclosed herein. In some embodiments, a test and a retest is an examination or procedure using one or more specialized machine as disclosed herein. In some embodiment, a test or a retest is a same test with all testing conditions substantially identical for the test and the retest except the time of testing. In further embodiments, the testing conditions include one or more selected from: the testing subjects, the testing instruments, the testing procedure, the testing method, the result recording method, the testing time, the testing artifacts, and the testing noise level. In some cases, the testing conditions include one or more selected from: a test processing method, a test evaluation method and a test scoring method. In some cases, a test and a retest is performed with only one or more differences in testing conditions. As a nonlimiting example, the only substantial difference between testing conditions in a test and a retest may be the testing time. In some embodiments, a test or a retest is a same test with an identical testing protocol except the time of testing. In some cases, a test and a retest is performed with one or more differences in testing conditions. As a nonlimiting example, a test and a retest is performed before and after at least one therapeutic intervention, respectively, and also with different testing time. In some embodiments, a test and a retest is performed before and after at least some disease progression has taken place, respectively. In some embodiments, a test and a retest is a different test.

In some cases, a test or a retest as disclosed herein may be any suitable vision tests or medical tests that can be described in a feature space. As nonlimiting examples, a test or a retest may be one or more selected from: an acuity test, an acuity threshold test, an acuity slope test, a sensitivity test, a perimetry test, a color sensitivity test, a spatial frequency sensitivity test with at least one spatial frequency ranging from 0 cycles per degree of visual angle (cpd) to 50 cpd, a contrast sensitivity test, a contrast sensitivity function (CSF) test, a CSF test with at least one spatial frequency ranging from 0 to 50 cpd, a peak spatial frequency test, a peak sensitivity test, a sensitivity bandwidth test, an optical coherence tomography (OCT) test, a ultrasound test, a magnetic resonance imaging (MRI) test, an X-ray test, a microscopic test, a computerized adaptive contrast sensitivity test using a computerized contrast sensitivity testing device, a qCSF test using a qCSF testing device, or any other imaging modality. In some embodiments, a test or a retest examines at least one preselected parameter of at least a vision disease. In some embodiments, a test or a retest examines at least one preselected parameter of at least one therapeutic treatment or intervention.

In some cases, the test may be the first test being performed on the subject(s). Alternatively, the test may be a test preceding a number of retests. Alternatively, a test may be any test that proceeds or follows a certain number of retests. In some cases, each subject may have one or more retests. In further cases, the number of retests for each subject may or may not be identical. As a nonlimiting example, four human subjects may each have a test; three of the four subjects may have 3 retests each; the last subject may have 2 retests. The total number of subjects is 4, and the total number of retests may be 11. A test and a retest may be in the same feature space. Alternatively, a test and a retest may be in two different feature spaces.

In some cases, a test (retest) may not be limited to vision test. In some cases, a test (retest) may be any suitable test of physiological functions or pathological functions. In some cases, a test (retest) may be any suitable tests that may be described in a feature space.

Results

In some embodiments, at least one test and at least one retest is performed with a same subject. In some embodiments, a test and a retest includes at least one test result and a retest result. In some embodiments, a test and a retest includes at least a number of test results and a number of retest results, the number being any real number no smaller than 1. In some embodiments, a test result or a retest result is indicative of visual performance of a subject. In some embodiments, a test result or a retest result is indicative of at least one disease progression. In some embodiments, a test result or a retest result is indicative of effect of at least one therapeutic intervention.

In some embodiments, a test result or a retest result includes at least one test score. In some embodiments, a test (retest) score is a scalar. In further embodiments, a test (retest) result includes a score ranging anywhere from 0 to 1. In some embodiments, a test (retest) score is normalized by the maximum score or a pre-selected number to be within the range of 0 to 1. In some embodiments, a test (retest) score is any non-negative real number. In some embodiments, a test (retest) score is one or more real numbers. In some embodiments, a test (retest) score is multi-dimensional. In some embodiments, a test (retest) score is a vector. In some embodiments, a test (retest) score is a multi-dimensional vector. In some embodiments, the number of dimensions of a test (retest) score is determined by or equal to the number of dimensions of a feature space. In some embodiments, a test (retest) score includes at least one scalar score for each dimension in the feature space that a test and a retest was performed and/or measured.

In some embodiments, a test (retest) score in at least one dimension is weighted. In some embodiments, a test (retest) score or the raw data of a test or a retest is processed in at least one dimension. In some embodiments, the processing of a test (retest) score includes one or more selected from weighting, normalization, noise reduction, filtering, translation, quantization, and rounding up.

In some cases, a test or a retest as disclosed herein may be any suitable vision tests or medical tests that may be conducted on specialized medical machinery other than a generic computer. In some embodiments, a test (retest) result may be collected from a specialized machine that enables measurement of visionary parameters of human subjects. In some embodiments, the methods and systems, and digital processing devices as disclosed herein include a connection to one or more specialized machinery that enables measurement of visionary parameters of human subjects. In some embodiments, the specialized machinery disclosed herein may include but are not limited to: a computerized adaptive contrast sensitivity testing device, a qCSF testing device, an OCT machine, a Mill machine, a X-ray machine, an ultrasound machine, a visual field testing machine, a fundus photography system, a dark adaptation measurement machine, an auto-refractor machine, a frequency-doubling technology machine, a tonometer machine, an aberrometer machine, an eye-tracking device, an Adaptive Sensory Technology Sentio device ("Next-generation vision testing: the quick CSF" in Current Directions in Biomedical Engineering 2015; 1:131-134 by Don et. al.), and an ocular alignment machine. In some embodiments, the specialized vision test machine may not include a vision acuity chart. In some cases, there may be a wired or a wireless connection between the specialized machinery used to collect test (retest) results. In some embodiments, the wired or wireless connection may be direct. In other cases, the connection may be indirect, and the collected result(s) of raw data may be preprocessed at another machine using preprocessing steps as disclosed herein. In some embodiments, the methods and systems disclosed herein may include a processor or a digital processing device for preprocessing of raw data collected from a one or more specialized machines.

In some cases, the methods and systems as disclosed herein receive test results from the specialized machinery via one or more connection selected from: a network, an Ethernet, an Internet, a cable, a phone line, a non-transitory computer-readable media, an online cloud, a database, a phone line, an aux connection, a Bluetooth connection, a aux connection, or the like.

Test-Retest Precision

In some embodiments, test-retest similarity, test-retest precision, test-retest reliability, and test-retest repeatability are interchangeable or equivalent as disclosed herein. In some embodiments, test-retest similarity, test-retest precision, test-retest reliability, and test-retest repeatability indicate how similar the test-retest results are. In some cases, the test-retest reliability helps determine if the difference in test-retest is of medical significance or not. In some cases, the test-retest reliability helps determine if the difference in test-retest is caused by testing noise, testing errors, and or any other factors unrelated to medical conditions or therapeutic interventions.

In some embodiments, the test-retest precision is a measure of how similar a test-retest(s) pair is. In some embodiments, the test-retest precision is an assessment of the similarity of test-retest results from one subject. In some embodiments, the test-retest precision is an assessment of the similarity of test-retest results from more than one subject, with the test-retest precision assessed for each of the subjects so each subject is the "one subject" once in a test-retest precision measurement. Each test-retest pair may include one test and one retest for the same subject. Each test-retest pair may include one test and one retest for two different subjects.

Each test-retest pair may include one test and more than one retest of the same subjects. Each test-retest pair may include one test result and more than one retest results of the same subjects.

In some embodiments, CoR or the Bland-Altman CoR is calculated as $$CoR = 1.96\sqrt{\frac{1}{N-1}\sum_{n=1}^{N}\left[x_{n,2} - x_{n,1} - \frac{1}{N}\sum_{m=1}^{N} x_{m,2} - x_{m,1}\right]^2},$$

wherein each subject $x_n$ has a test-retest pair, $x_{n,1}$ and $x_{n,2}$, and the total number of subject is N.

In some embodiments, ICC is calculated as $$ICC = \frac{2}{\sum_{n=1}^{N}(x_{n,1}-\bar{x})^2 + \sum_{n=1}^{N}(x_{n,2}-\bar{x})^2}\sum_{n=1}^{N}(x_{n,1}-\bar{x})(x_{n,2}-\bar{x})$$

wherein each subject $x_n$ has a test-retest pair, $x_{n,1}$ and $x_{n,2}$, the total number of subject is N, and wherein $$\bar{x} = 1/(2N)\Sigma_{n=1}^{N} x_{n,1} + x_{n,2}.$$

Vision-Based Features

In some embodiment, a vision based feature is any feature that may be tested or examined using a vision-related testing device. In some embodiments, non-limiting examples of a feature include but is not limited to one or more selected from: a retinal layer thickness, a retinal blood vessel thickness, a retinal haemorrhage index, a structural descriptor of an image of the eye, a cup-to-disc ratio, a drusen count, an edema count, a frequency doubling technology-related feature, a perimetry subfield threshold, a visual field loss summary statistic, a visual field sensitivity map, an interocular pressure, a saccadic latency, a smooth pursuit gain index, a dark-adaptation rod intercept time, a chromatic contrast threshold, and a temporal frequency threshold. In some embodiments, non-limiting examples of features include one or more selected from: a parameter of acuity, an acuity threshold, an acuity slope, a sensitivity parameter, a sensitivity parameter of CSF, a CSF distribution, a probability distribution of CSF, the peak spatial frequency fmax of CSF, peak sensitivity γmax of CSF, bandwidth β of CSF, and a low-frequency truncation parameter δ of CSF, a sensitivity parameter of quick CSF (qCSF), qCSF, a qCSF distribution, a joint distribution of qCSF over four parameters (a distribution of results in a four-dimensional space, with each result describing a CSF curve and each curve living in a two-dimensional space of spatial frequency and contrast), an area under the Log CSF (AULCSF) integrated over the spatial frequency range from at least 1.5 to 18 cycles per degree (cpd), a CSF acuity, as a non-limiting example, the spatial frequency point where the CSF described by four parameters reaches a contrast threshold of 100%, a sensitivity threshold of the CSF that is described by four parameters for at least one spatial frequency ranging from 1 to 50 cpd, and the spatial point for which the CSF reaches a pre-determined contrast threshold.

In some embodiments, a contrast threshold is the inverse of sensitivity. In some embodiments, the four parameters of CSF or qCSF are a peak spatial frequency fmax of CSF, peak sensitivity γmax of CSF, bandwidth β of CSF, and a low-frequency truncation parameter δ of CSF. In some embodiments, the at least one spatial frequency ranging from 1 to 18 cpd includes at least 1 cpd, 1.5 cpd, 3 cpd, 6 cpd, 12 cpd, and 18 cpd. In some embodiments, AULCSF represents the median, average, or processed AULCSF computed over spatial frequencies ranging from 1.5 cpd to 18 cpd. In some embodiments, the CSF is a curve in a two dimensional space of spatial frequency and contrast.

In further embodiments, a feature includes at least one transformation or an operation of at least one vision feature. In some embodiments, a transformation or an operation includes one or more selected from: a mean, a median, a standard deviation, a multiplication by a pre-selected number or another feature, a square, a cube, a nth order multiplication, a square root, a nth root, a division by a pre-selected number, a random subsampling, a Fourier Transform, a rounding, and a change in quantization level.

In some embodiments, a feature includes a probability or statistical distribution of at least one feature. In some embodiments, a feature includes a joint probability or statistical distribution of at least two features. In some embodiments, a feature includes information derived from a probability distribution, a statistical distribution of one feature, a joint probability distribution of at least two features, a joint statistical distribution of at least two features. In some embodiments, a feature includes a scalar feature.

In some embodiments, the methods and systems disclosed herein includes a feature space. In some embodiments, a feature space includes any combination of the above-mentioned features and/or transformations, where each feature corresponds to one dimension in a multi-dimensional space.

In some embodiments, the feature space includes a dimension size no less than one. In some embodiments, at least a number of dimensions in the feature space are orthogonal to each other, the number being no less than 2.

In some embodiments, the feature space undergoes another transformation that scales and rotates the coordinate system of the feature space. As a non-limiting example, individual dimension (feature) is scaled with different factors to make the range of feature values comparable. In some embodiments, the coordinate system is rotated by a whitening step that de-correlates the features. In some embodiments, a principle component analysis (PCA) is applied that de-correlates the features and reduces the dimensionality of the feature space to preserve only the principle components of the feature space. In some embodiments, a test result is represented in a feature space as one multi-dimensional vector, or as a distribution of multi-dimensional vectors.

In some embodiments, in the visual domain, the predominant tool for functional assessment is acuity, which measures the smallest size of a stimulus (typically, a letter) that an observer can recognize at full contrast. In some embodiments, while acuity is well established and can be very useful e.g. for adjusting optical correction, it has at least two issues in domains where precision is paramount, such as in clinical trials. First, the variability of repeated measurements makes the method insensitive to subtle changes in vision, e.g. due to disease progression or treatment. Second, some ophthalmic and neurologic conditions affect acuity only moderately, despite of effects on visual function. In some embodiments, the contrast sensitivity function (CSF) relates an observer's ability to recognize a spatial pattern not only to its size, but also to its contrast. In some embodiments, comparing to acuity, the CSF correlates better with performance in visually guided everyday activities, for non-limiting examples, driving, walking, and the ability to recognize faces.

Traditional tests such as paper charts typically only return one number (e.g. "20/20 vision", i.e. 100%). In some embodiments, for more complex tests such as the qCSF, which returns joint probability distributions over four parameters (a distribution of test results in a four-dimensional space, with each result describing a CSF curve, each of these curves living in a two-dimensional space of spatial frequency and contrast), an arbitrary number of features is generated based on these distributions to create a feature space of arbitrary dimensionality; for example, the median AULCSF is a one-dimensional feature space, and the combination of median AULCSF and median CSF acuity would give a two-dimensional feature space.

In some embodiments, visual sensitivity is comprehensively described by CSF, but current routine clinical care does not include its assessment because of the time-consuming need to estimate thresholds for a large number of spatial frequencies. In some embodiments, the quick CSF (qCSF) method dramatically reduces testing times by using a Bayesian information maximization rule. In some embodiments, the qCSF method uses a computationally intensive algorithm and optimizes stimulus selection by computing the expected information gain over a very large set of possible stimuli and the probability distribution of possible CSFs, given the history of previous trials. In some embodiments, the CSF is a description of visual function that assigns a contrast sensitivity (the most subtle gray/gray difference that can be discerned) to every possible spatial frequency (size of the stimulus), thus, the CSF space is two-dimensional (contrast and spatial frequency). People have measured the full CSF before, but the combinatorial complexity of the additional dimension made those tests impractical for clinical care—they took 30-60 minutes; the method developed by Lesmes and colleagues, however, reduced testing times to 2-3 minutes (Lesmes et. al. "Bayesian adaptive estimation of the contrast sensitivity function: The quick CSF method," Journal of Vision 2010 10(3) hence the 'quick' CSF).

In some embodiments, the quantization level may be changed by changing the number of digits in a test and a retest score. In other embodiments, the quantization level is not changed by changing the number of digits but may be determined by the number of different test scores that can result from the test. As an example, a test with three scores, $\frac{1}{3}$, $\frac{1}{7}$, and 1, even with infinite number of digits the test itself provides only three scores thus only very quantized outcomes. In some embodiments, the number of digits is the number of fractional digits. In some embodiments, at least two to at least 5 intermediate steps are included between two adjacent digits after the decimal point. In some cases, as a non-limiting example, a quantization level with 5 fractional digits is less coarse and less quantized than a quantization level with 4 fractional digits given that the fraction digits are for an identical digit after the decimal point. In some embodiments, as a non-limiting example, with 5 fractional steps for the second digit after the decimal point, 1.028 is rounded to 1.02 and 1.071 is rounded to 1.08).

Similarities

The methods and systems disclosed herein, in various embodiments, are applied in order to evaluate similarity, repeatability, reliability, precision, or variability of a test-retest pair. In some cases, the similarity, repeatability, reliability, precision, or variability of a test-retest pair is equivalent or interchangeable as disclosed herein.

In some cases, the similarity of a test-retest pair is assessed by ranking distances between the selected test result and each retest result of the plurality of subjects and obtaining a rank of the distance from the selected test result to the retest result of the same subject. As a nonlimiting example in FIG. 1, a similarity of test-retest pair of subject 2 (left) is lower than the similarity of test-retest pair of subject 3 (right), as the distance of test-retest pair of subject 2 (left) ranks 3 out of 4 while the distance of test-retest pair of subject 3 (right) ranks 1 out of 4. A rank precision may be obtained based on the similarities. In this case, the rank precision for subject 2 using MAP is $\frac{1}{3}$ and the rank precision for subject 3 using MAP is 1.

Ranks

In some embodiments, the method described herein includes a rank. In some embodiments, a rank is given to each retest result. Further, each retest result may include one or more retests for each of the plurality of subjects participated in the test-retest precision measurement. In some embodiments, a rank is a real number ranging from 0 to N−1, wherein N is the total number of subjects, the total number of retests, the total number of tests, or the total number of tests and retests. In some embodiments, a rank is a real number ranging from 1 to N, wherein N is the total number of subjects, the total number of retests, the total number of tests, or the total number of tests and retests. In some embodiments, the rank is given to each retest according to a distance of each retest to at least one specified test. As a nonlimiting example, a total of 6 subjects each have one test and two retests results. A rank may be given to each of the 12 retest results based on their distance to the test of the first subject.

Other example of ranks may be seen in FIG. 1. Referring to FIG. 1, in a particular embodiment, four subjects are measured in a test-retest event and test-retest precision is evaluated. In this embodiment, test and retest scores for each of the four subjects are plotted, and the distance of each retest result to the test result of subject 2 (left panel) and subject 3 (right panel) is obtained. Correspondingly, in the same embodiment, the rank of distance is optionally calculated. In this embodiment, for subject 2, retest score has a rank of 3 in a total number of 4 subjects, so that the average precision of subject 2's retest is the inverse of rank of the retest, thus, the precision is $\frac{1}{3}$. In the same embodiment, similarly, for subject 3, retest score has a rank of 1 in a total number of 4 subjects, so that the average precision of subject 3's retest is the inverse of rank of the retest, thus, the precision is 1.

In some embodiments, the rank number is reversibly related to the distance value. As a non-limiting example, the retest result with the shortest distance to at least one specified test result has a rank of 0; the retest result with the longest distance to at least one specified test result has a rank of N−1. In some embodiments, the retest results and/or subjects of the retest results are sorted in a list with the corresponding distance in a monotonically non-descending order: the retest result and/or subject at the top of the sorted list has a rank of 0; the retest result and/or subject at the bottom of the sorted list has a rank of N−1. In some embodiments, the rank is normalized by the total number of subjects. In some embodiments, the rank is weighted given preselected weighting for at least one rank value.

In some embodiments, a rank is any number ranging from 1 to N, wherein N is the total number of subjects, the total number of retest, or the total number of tests. In some embodiments, the rank number is reversibly related to the distance value. As a non-limiting example, the retest result with the shortest distance to at least one specified test result has a rank of 1; the retest result with the longest distance to at least one specified test result has a rank of N. In some embodiments, the retest results and/or subjects of the retest results are sorted in a list with the corresponding distance in a monotonically non-descending order: the retest result and/or subject at the top of the sorted list has a rank of 1; the retest result and/or subject at the bottom of the sorted list has a rank of N.

In some embodiments, the rank is the same for at least two retest results if the distance is identical for at least two retest results and/or subjects. In some embodiments, the identical rank is calculated as an average of adjacent ranks which would be given to the at least two retest results if they were not identical without affecting the ranks of other retest results. In some embodiments, as a non-limiting example, distances of 0.1, 0.1, 0.2, and 0.3 get ranked as 1.5, 1.5, 3, and 4, respectively.

Mean Average Precision (MAP) and Fractional Rank Precision (FRP)

The methods and systems disclosed herein may include one or more suitable test-retest precision measurement methods. In some embodiments, the methods and systems disclosed herein include a MAP or a FRP calculation for the evaluation of test-retest precision, test-retest repeatability, test-retest reliability, or test-retest variation. In some cases, the methods and systems disclosed herein may include a combination of MAP and FRP calculation, the weighting of MAP or FRP calculation may be preselected based on empirical experience, simulation, trails, or any other suitable factors.

In some cases, fractional rank precision may not be limited to non-integer ranking to break ties. In some cases, fractional ranking may also include normalized ranking precision or normalized ranking. In some embodiments, fractional ranking is equivalent to and interchangeable with normalized ranking. In some embodiments, fractional ranking precision is equivalent to and interchangeable with normalized rank precision (NRP).

In some embodiments, with one test and one retest for each subject, rank precision is directly calculated as (1−rank (Ri)/N), wherein the rank goes from 0 to N−1, wherein N is the total number of subjects, and wherein i is the selected subject.

In some embodiments, the FRP is the mean of the rank precision for each subject of all the subjects in a test-retest event.

In some embodiments, with at least one test and at least one retest for each subject, the average precision (AveP) is directly calculated as 1/rank (Ri), wherein rank goes from 1 to N, wherein N is the total number of subjects, and i is the selected subject. The average precision may be interchangeable or equivalent to the ranks precision in various embodiments as disclosed herein. In some embodiment, each subject has more than one test results and more than one retest result, and the AveP is the average of 1/rank(Ri) for each retest of the selected subject, wherein i is the selected subject. In some embodiments, the MAP is the mean of AveP for each subject of all the subjects in a test-retest event.

In some embodiments, the MAP is calculated as $$MAP = \frac{1}{N}\sum_{n=1}^{N} Precision_{x_{n,1}}(x_{n,2}),$$

wherein each subject $x_n$ has a test-retest pair, $x_{n,1}$ and $x_{n,2}$, the total number of subjects is N, and wherein precision of a test result $x_n,1$ is based on the rank of its corresponding retest $x_{n,2}$ as $$Precision_{x_{n,1}}(x_{n,2}) = \frac{1}{rank_{x_{n,1}}(x_{n,2})}.$$

In some embodiments, the FRP is calculated as $$FRP = 1 - \frac{1}{N}\sum_{n=1}^{N} \frac{rank_{x_{n,1}}(x_{n,2}) - 1}{N},$$

wherein each subject $x_n$ has a test-retest pair, $x_{n,1}$ and $x_{n,2}$, the total number of subjects is N.

In some embodiments, the methods and systems disclosed herein include one or more recursive steps. In further cases, one or more recursive steps repeats only once for each of the plurality of subjects. In further cases, one or more recursive steps repeats for more than once for each of the plurality of subjects when each subject has more than one retest results, the repetition number being equal to the number of retests for individual subjects.

Distances

In some embodiments, the distance between test-retest results is represented by a number, or a multi-dimensional vector. In some embodiments, the distance may be any distance calculated using any suitable calculation methods for two scalars or vectors representing the test-retest results pair in one or two feature spaces. In some embodiments, a distance is one or more selected from: the Euclidean distance, the Mahalanobis distance, and the Manhattan distance. In some embodiments, the Manhattan distance represents a sum of dimension-wise absolute differences.

In some embodiments, the distance between test results is represented by one or more selected from: the distributions of multi-dimensional vectors, the mean, the median, or other quantiles of the distribution of Euclidean or Manhattan distances between the vectors. In some embodiments, the distance between test-retest results is represented by the mean, median, or any other quantiles of the distribution of Mahalanobis distances between sampled points of the one distribution and the whole other distribution. In some embodiments, the Mahalanobis distance expresses distance in terms of the width of the data ellipsoid in the multi-dimensional feature space.

Referring to FIG. 1, in a particular embodiment, four subjects are measured in a test-retest event and test-retest precision is evaluated using MAP. In this embodiment, test and retest scores for each of the four subjects are plotted, and the distance of each retest result to the test result of subject 2 (left panel) and subject 3 (right panel) is obtained. Correspondingly, in the same embodiment, the rank of distance is optionally calculated. In this embodiment, MAP for all four subjects is optionally calculated as the mean of average precision for each of the four subjects. In this case, MAP of all four subjects is 0.708.

Figure 2:
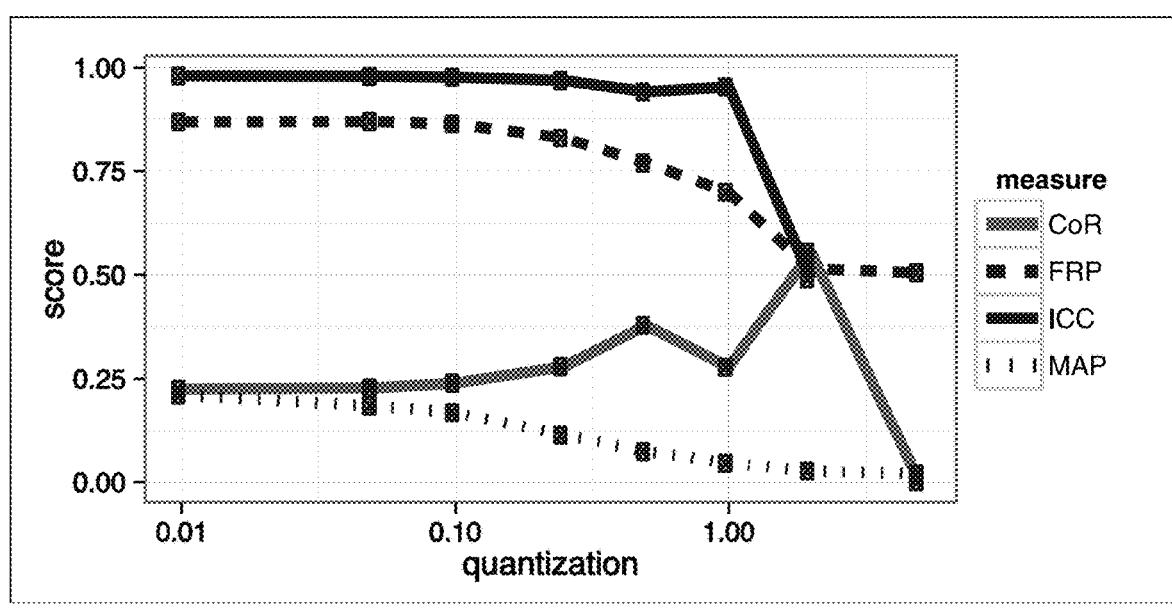
FIG. 2 shows a non-limiting example of effect of quantization of area under log of contrast sensitivity function (AULCSF) score on test-retest reliability measured by CoR, ICC, FRP, and MAP.

Referring to FIG. 2, in a particular embodiment, effect of quantization of test and retest scores on different of test-retest precision (TRP) measures is examined. In this embodiment, a median AULCSF computed over spatial frequencies from 1.5 cpd to 18 cpd is measured using different test-retest precision measures. In this embodiment, the quantization level affects accuracy in test-retest precision measures including CoR, ICC, FRP, and MAP (FIG. 2). In this embodiment, MAP precision score, which reflects measurement precision using MAP, gradually decreases monotonically with increased quantization. Additionally, in the same embodiment, coarse quantization that renders a test uninformative may lead to 'perfect' reliability as measured by CoR and ICC. For example, when quantization level is less than 1, ICC may show an inaccurately high precision score. In this embodiment, for intermediate quantization level of about 0.10 to about 1.00, MAP is more sensitive and accurate than ICC.

Figure 3:
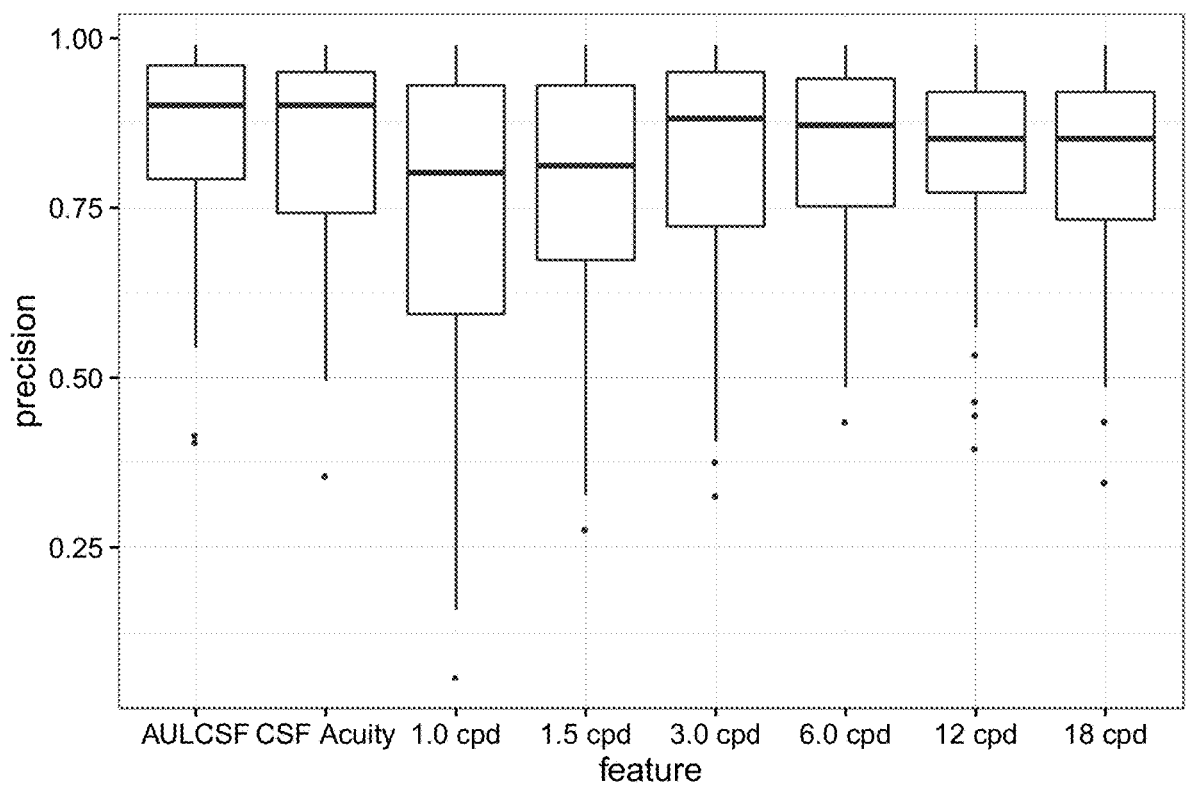
FIG. 3 shows a non-limiting example of the fractional rank precision method disclosed herein; in this case, the test-retest precision distributions across subjects for different vision sensitivity features.

Referring to FIG. 3, in a particular embodiment, boxplots of the distributions of FRP are plotted over the subjects for various visionary features. The mean of the distribution represents the TRP value for various visionary features. In this embodiment, using FRP measure, test-retest precision may be different when it is based on different vision-based feature. AULCSF may be slightly more accurate with a high average precision while 1.0 cpd may have a lower test-retest precision.

Figure 4:
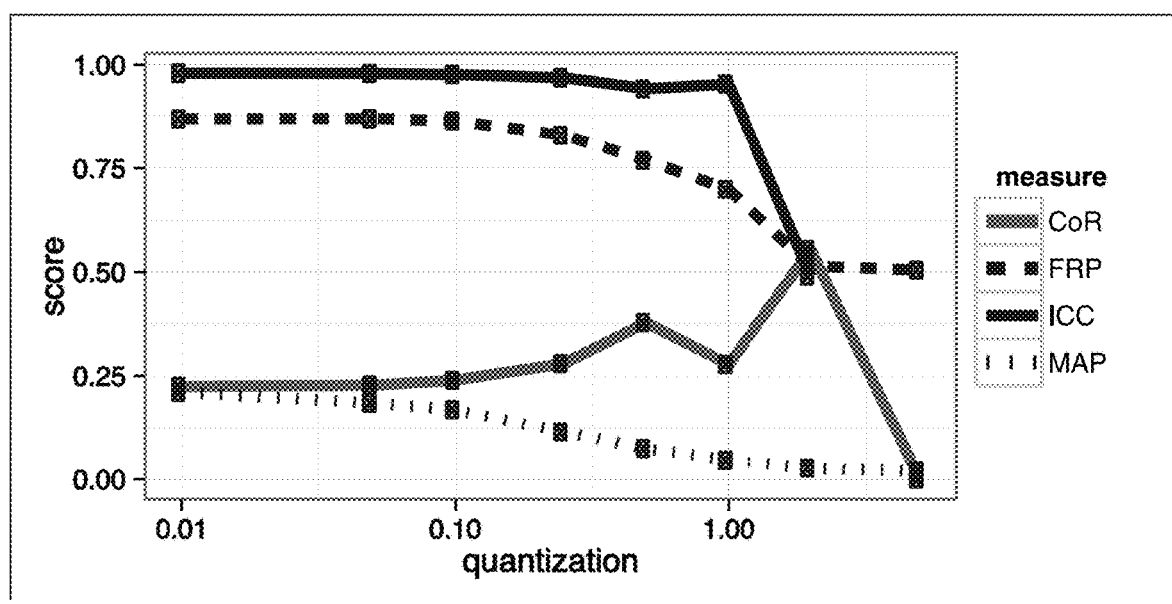
FIG. 4 shows a non-limiting example of effect of quantization of area under log of contrast sensitivity function (AULCSF) score on test-retest reliability measured by CoR, ICC, FRP, and MAP.

Referring to FIG. 4, in a particular embodiment, effect of quantization on different test-retest precision measures is examined. In this embodiment, a median AULCSF computed over spatial frequencies from 1.5 cpd to 18 cpd is measured using different test-retest precision (TRP) measures. These different measures include CoR, ICC, MAP, and FRP. In this embodiment, CoR is particularly vulnerable to quantization differences and shows non-monotonic behavior with increased level of quantization. In the same embodiment, the ICC also behaves non-monotonically with increased level of quantization. In the same embodiment, the change of FRP evaluation of precision stays monotonic as the level of quantization increases. In this embodiment, the quantization level affects the accuracy in test-retest precision measures including CoR, ICC, MAP, and FRP.

Figure 7:
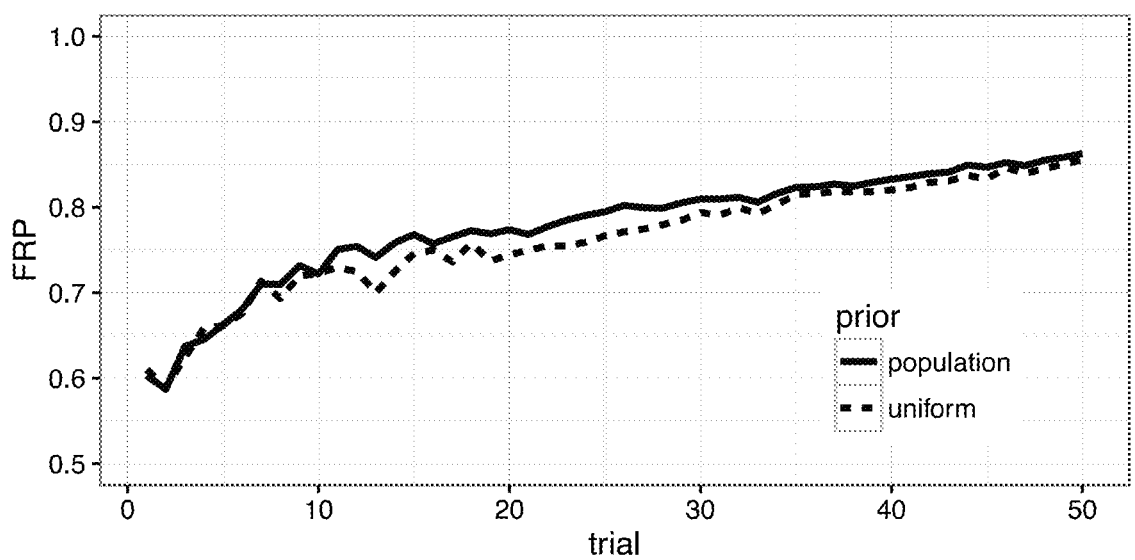
FIG. 7 shows a non-limiting example of the fractional rank precision method disclosed herein; in this case, fractional rank precision over the time course for different priors in quick CSF (qCSF) analysis initialization.

Referring to FIG. 7, in a particular embodiment, the effect of choosing a different prior over the CSF search space on FRP, is determined as a function of trial number. In this case, both the uniform and the population prior lead to very similar FRP results over the first few trials, as only very little information about the true CSF is available. In the same embodiments, for the time range between 10 to 30 trials, the analysis initialized with the population prior shows better convergence, In the same embodiment, for the time range after 30 trials, the difference between FRP diminishes as both approaches converge; however, there is still a small benefit for population after 50 trials (FRP of 0.871 and 0.864, respectively).

Digital Processing Device

In some embodiments, the platforms, systems, media, and methods described herein include a digital processing device, or use of the same. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 8:
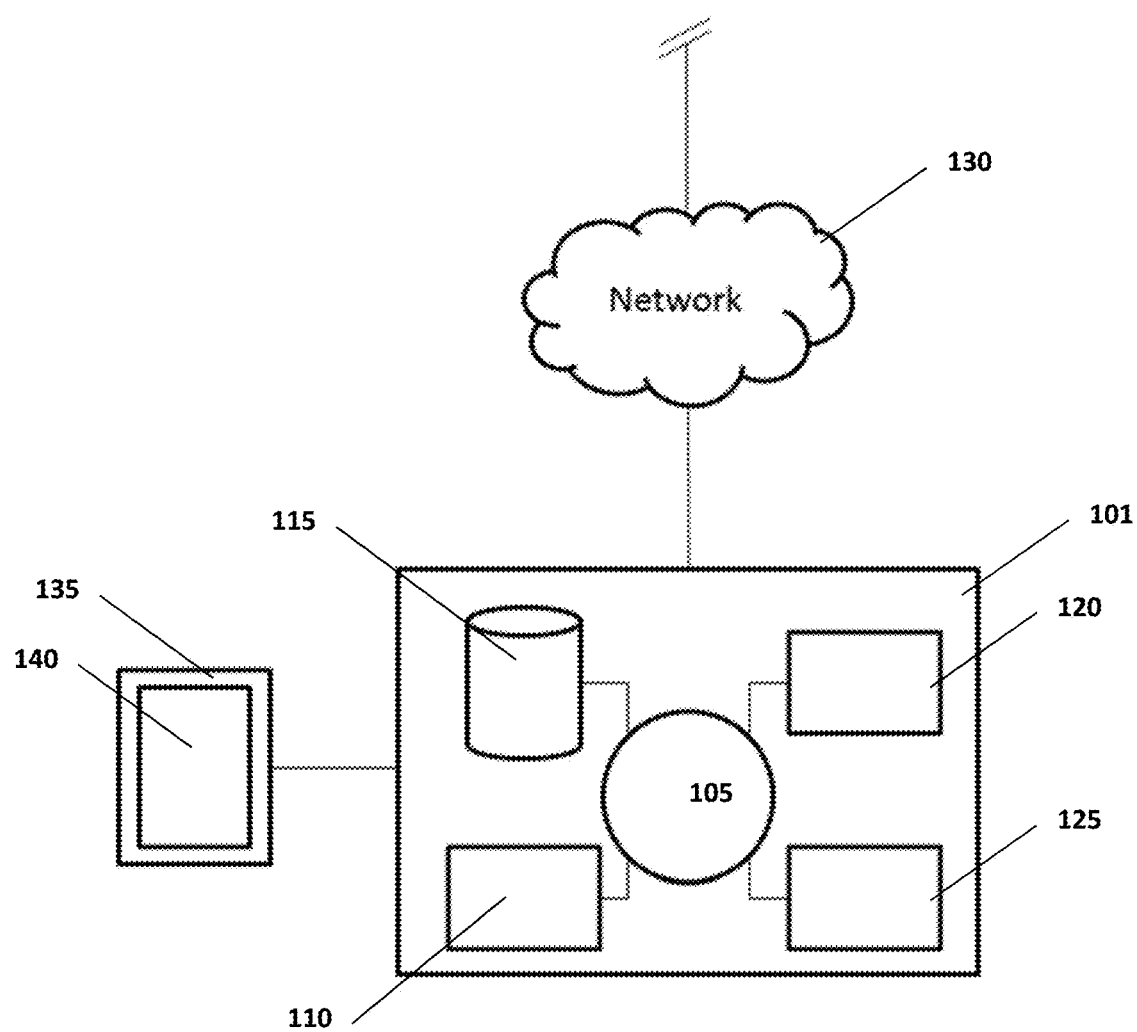
FIG. 8 shows a non-limiting exemplary embodiment of a digital processing device as disclosed herein.

Referring to FIG. 8, in a particular embodiment, an exemplary digital processing device 101 is programmed or otherwise configured to measure test-retest reliability using FRP, MAP or other suitable precision evaluation methods. The device 101 can regulate various aspects of test-retest precision measurement of the present disclosure, such as, for example, formulating test-retest reliability as an information retrieval problem, and ranking retest measurements by their distance to a subject's test measurement. As another example, it may assess a similarity between a test result and a retest result. In this embodiment, the digital processing device 101 includes a central processing unit (CPU, also "processor" and "computer processor" herein) 105, which can be a single core or multi core processor, or a plurality of processors for parallel processing. The digital processing device 101 also includes memory or memory location 110 (e.g., random-access memory, read-only memory, flash memory), electronic storage unit 115 (e.g., hard disk), communication interface 120 (e.g., network adapter) for communicating with one or more other systems, and peripheral devices 125, such as cache, other memory, data storage and/or electronic display adapters. The memory 110, storage unit 115, interface 120 and peripheral devices 125 are in communication with the CPU 105 through a communication bus (solid lines), such as a motherboard. The storage unit 115 can be a data storage unit (or data repository) for storing data. The digital processing device 101 can be operatively coupled to a computer network ("network") 130 with the aid of the communication interface 120. The network 130 can be the Internet, an internet and/or extranet, or an intranet and/or extranet that is in communication with the Internet. The network 130 in some cases is a telecommunication and/or data network. The network 130 can include one or more computer servers, which can enable distributed computing, such as cloud computing. The network 130, in some cases with the aid of the device 101, can implement a peer-to-peer network, which may enable devices coupled to the device 101 to behave as a client or a server. The digital processing device 101 can be operatively connected to one or more specialized medical device (not shown) via the network 130. Such connection may enable data collection from the medical device; the data may include one or more test results, retest results, and other related test and subject information. The specialized medical device is configured to measure visionary features(s) of one or more subjects.

Continuing to refer to FIG. 8, the CPU 105 can execute a sequence of machine-readable instructions, which can be embodied in a program or software. The instructions may be stored in a memory location, such as the memory 110. The instructions can be directed to the CPU 105, which can subsequently program or otherwise configure the CPU 105 to implement methods of the present disclosure. Examples of operations performed by the CPU 105 can include fetch, decode, execute, and write back. The CPU 105 can be part of a circuit, such as an integrated circuit. One or more other components of the device 101 can be included in the circuit. In some cases, the circuit is an application specific integrated circuit (ASIC) or a field programmable gate array (FPGA).

Continuing to refer to FIG. 8, the storage unit 115 can store files, such as drivers, libraries and saved programs. The storage unit 115 can store user data, e.g., user preferences and user programs. The digital processing device 101 in some cases can include one or more additional data storage units that are external, such as located on a remote server that is in communication through an intranet or the Internet.

Continuing to refer to FIG. 8, the digital processing device 101 can communicate with one or more remote computer systems through the network 130. For instance, the device 101 can communicate with a remote computer system of a user. Examples of remote computer systems include personal computers (e.g., portable PC), slate or tablet PCs (e.g., Apple iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 101, such as, for example, on the memory 110 or electronic storage unit 115. The machine executable or machine readable code can be provided in the form of software. During use, the code can be executed by the processor 105. In some cases, the code can be retrieved from the storage unit 115 and stored on the memory 110 for ready access by the processor 105. In some situations, the electronic storage unit 115 can be precluded, and machine-executable instructions are stored on memory 110.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome Web Store, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-In

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™ PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS Browser, Mozilla® Firefox® for mobile, Microsoft® Internet Explorer® Mobile, Amazon Kindle Basic Web, Nokia Browser, Opera Software Opera Mobile, and Sony® PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of information including one or more selected from: one or more of subjects, one or more test types, one or more retest types, one or more test results associated with each subject, one or more retests associated with each subject, and one or more features for the test/retest results. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

Incorporation by Reference

All publications, patents, and patent applications mentioned in this specification are herein incorporated by reference to the same extent as if each individual publication, patent, or patent application was specifically and individually indicated to be incorporated by reference.

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

EXAMPLES

The following illustrative examples are representative of embodiments of the software applications, systems, and methods described herein and are not meant to be limiting in any way.

Example 1

Comfortably seated, subjects holding an iPad 4 that is set to a mean screen luminance of 185 cd/m2 at a viewing distance of 60 cm. In each vision test-retest trial, a randomly chosen bandpass-filtered Sloan letter is presented for 500 ms, and the subject then had to register their response by touch-selecting a letter from an array on the screen (10-Alternatives Forced Choice). The stimulus space is log-spaced and comprised 24 spatial scales (0.64 to 41 cycles per degree (cpd)) and 48 contrast levels (0.2 to 100%). In order to avoid uninformative regions of the stimulus space, the next stimulus was then randomly chosen from the top 10 percent of the distribution of expected information gain. All subjects run the test multiple times. Controls are tested monocularly in both eyes and binocularly; to estimate reliability of the procedure, one of these three conditions (randomly chosen) is repeated. Myopes are tested both with and without their optical correction, with one repeat, for a total of 7 conditions. We report only on the repeated data.

Two traditional methods, ICC and CoR are compared with the FRP method described herein for their measurements of the test-retest precision of different features for vision sensitivity testing. Such vision sensitivity testing features include AULCSF, which is the area under the log CSF integrated between spatial frequencies from 1.5 to 18 cpd, the CSF acuity, and the sensitivity threshold of CSF at six different spatial frequencies including 1 cpd, 1.5 cpd, 3 cpd, 6 cpd, 12 cpd, and 18 cpd. Results of comparison are shown in Table 1. As shown in FIG. 3, boxplots of the distributions of FRP are plotted over a plurality of subjects for various visionary features that may be included in a feature space. These various features are non-limiting examples of vision-based features that may be used to measure qualitative or quantitative aspects of human vision. The mean of the distribution represents the TRP value for each feature. FRP method disclosed herein indicates that AULCSF most precisely identifies test-retest pairs even though it summarizes over a broad range of spatial frequencies. Additionally, the sensitivity at 6 cpd has a much higher CoR, 0.293, than the CSF acuity feature, 0.193, but more precisely identifies test-retest pairs according to the FRP method disclosed herein, 0.848 vs. 0.844. The ICC is vulnerable to outliers: adding a single subject with very poor vision (for non-limiting example, test-retest sensitivity at 1.0 cpd of 0.1 and 0.05 respectively) substantially changes ICC from 0.868 to 0.817; while FRP is much less affected by outliers, and the change is less then 0.005.

Figure 5:
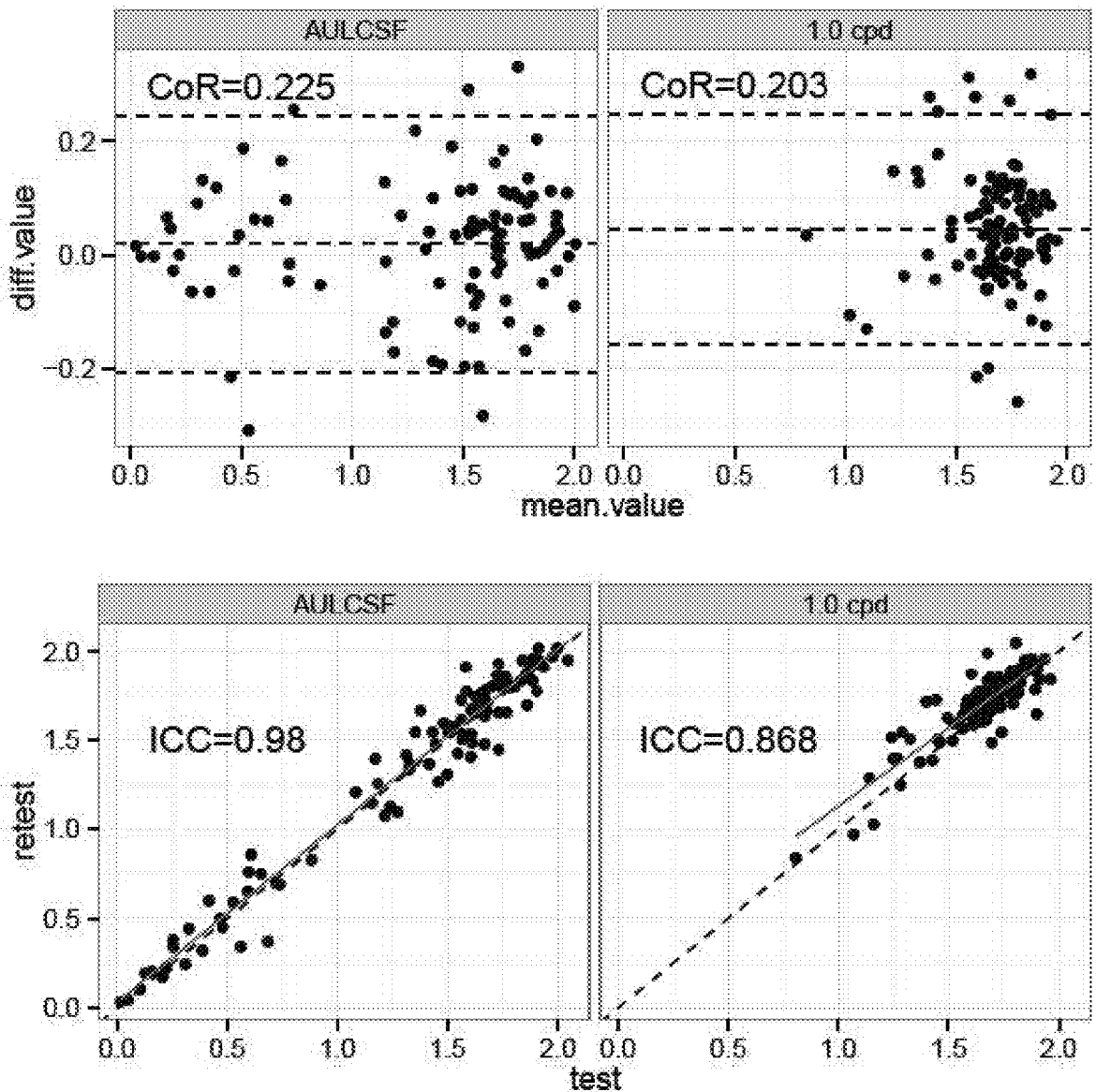
FIG. 5 shows non-limiting examples of evaluation for standard test-retest reliability methods, CoR and ICC.

Bland-Altman CoR and ICC for two selected features are graphically shown in FIG. 5.

TABLE 1

| Feature | ICC | CoR | FRP |
|---|---|---|---|
| AULCSF | 0.980 | 0.225 | 0.871 |
| CSF acuity | 0.967 | 0.193 | 0.844 |
| 1 cpd | 0.868 | 0.203 | 0.752 |
| 1.5 cpd | 0.945 | 0.196 | 0.793 |
| 3 cpd | 0.969 | 0.265 | 0.827 |
| 6 cpd | 0.975 | 0.293 | 0.848 |
| 12 cpd | 0.963 | 0.310 | 0.839 |
| 18 cpd | 0.917 | 0.369 | 0.823 |

Referring to FIG. 5, in a particular embodiment, test-retest precision is evaluated for test-retest scored using features including AULCSF and sensitivity of CSF at 1.0 cpd. In this embodiment, test-retest scores are compared using traditional Bland-Altman plot (top panels) and correlation plot (bottom panels). In this embodiment, dashed lines represent bias and 95% confidence intervals for test-retest differences. In this embodiment, the Bland-Altman plots do not show obvious dependencies of test-retest differences on the magnitude of the mean test score. The standard deviation of differences for 1.0 cpd is slightly smaller than for AULCSF. In the same embodiment, scatter correlation plots in the bottom panels also show strong agreement between test and retest scores.

Referring to Table 1, in a particular embodiment, fractional rank precision is calculated for different vision sensitivity features including AULCSF, which is the area under the log CSF between spatial frequencies from 1.5 to 18 cpd, the CSF acuity, and the sensitivity threshold of CSF at six different spatial frequencies including 1 cpd, 1.5 cpd, 3 cpd, 6 cpd, 12 cpd, and 18 cpd. In this embodiment, the AULCSF shows the largest area under the precision-recall curve, thus, the greatest fractional rank precision among all the examined features. In this embodiment, the AULCSF has the smallest test-retest variability and greatest test-retest precision.

Example 2

Figure 6:
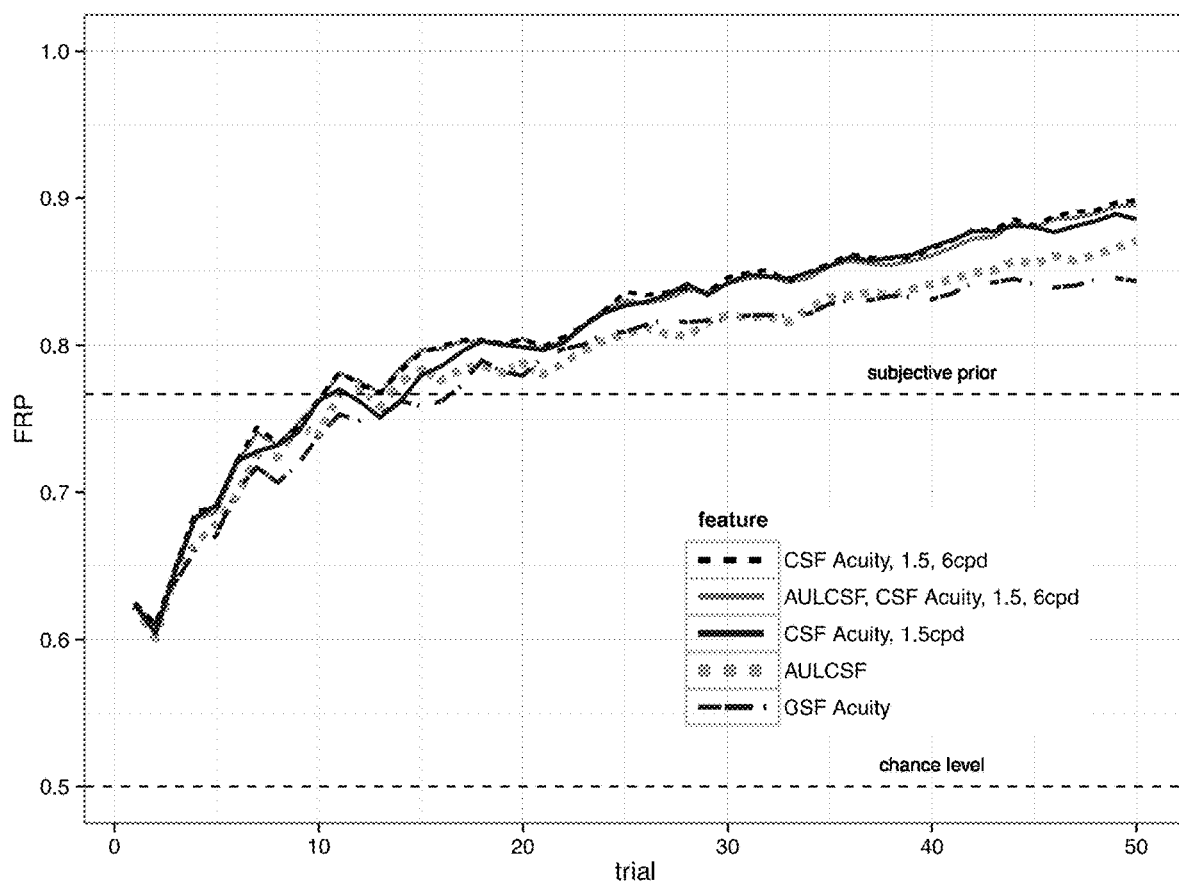
FIG. 6 shows a non-limiting example of the fractional rank precision method disclosed herein; in this case, fractional rank precision over the time course for different vision-based features.

Fractional rank precision values for different features of qCSF are examined in test-retest trials with multiple subjects. As shown in FIG. 6, with dashed lines indicating chance level (0.5) and FRP for subjective prior assessment (0.767). Among scalar features, the AULCSF yields higher FRP levels than CSF acuity (after 50 trials, FRP of 0.871 and 0.844, respectively) as it summarizes over a large range of spatial frequencies. Multi-dimensional features, however, identify test-retest pairs with greater precision. The combination of high-frequency cutoff (CSF acuity) and the sensitivity near the presumed peak of the CSF (1.5 cpd) already yields a FRP of 0.885; further adding sensitivity at a mid-range spatial frequency (6 cpd) improves FRP to 0.899, and the addition of the AULCSF results in the highest FRP of 0.901. Notably, FRP seems not to have plateaued after 50 trials for the multi-dimensional features indicating gain in precision is obtainable by running the qCSF method for more trials.

Example 3

Comfortably seated, subjects holding an iPad 4 that is set to a mean screen luminance of 185 cd/m2 at a viewing distance of 60 cm. In each vision test-retest trial, a randomly chosen bandpass-filtered Sloan letter is presented for 500 ms, and the subject then had to register their response by touch-selecting a letter from an array on the screen (10-Alternatives Forced Choice). The stimulus space is log-spaced and comprised 24 spatial scales (0.64 to 41 cycles per degree (cpd)) and 48 contrast levels (0.2 to 100%). In order to avoid uninformative regions of the stimulus space, the next stimulus was then randomly chosen from the top 10 percent of the distribution of expected information. All subjects run the test multiple times. Controls are tested monocularly in both eyes and binocularly; to estimate reliability of the procedure, one of these three conditions (randomly chosen) is repeated. Myopes are tested both with and without their optical correction, with one repeat, for a total of 7 conditions. We report only on the repeated data.

Two traditional methods, ICC and CoR are compared with the MAP method described herein for their measurements of the test-retest precision of different features for vision sensitivity testing. Such vision sensitivity testing features include AULCSF, which is the area under the log CSF between spatial frequencies from 1.5 to 18 cpd, the CSF acuity, and the sensitivity threshold of CSF at six different spatial frequencies including 1 cpd, 1.5 cpd, 3 cpd, 6 cpd, 12 cpd, and 18 cpd. Results of comparison are shown in Table 2. Among all the tested features, AULCSF yields highest MAP. In other words, AULCSF is the best feature to identify a pair of test-retest measurements, even though it summarizes over a broad range of spatial frequencies. Sensitivities for low spatial frequencies including 1 cpd and 1.5 cpd vary less across subjects, therefore are less discriminative across subjects.

TABLE 2

| Feature | ICC | CoR | MAP |
|---|---|---|---|
| AULCSF | 0.980 | 0.225 | 0.206 |
| CSF acuity | 0.967 | 0.193 | 0.200 |
| 1 cpd | 0.868 | 0.203 | 0.147 |
| 1.5 cpd | 0.945 | 0.196 | 0.185 |
| 3 cpd | 0.969 | 0.265 | 0.164 |
| 6 cpd | 0.975 | 0.293 | 0.149 |
| 12 cpd | 0.963 | 0.310 | 0.109 |
| 18 cpd | 0.917 | 0.369 | 0.110 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments, of the invention described herein may be employed in practicing the invention. It is intended that the following claims define the scope of the invention and that methods and structures within the scope of these claims and their equivalents be covered thereby.

What is claimed is:

1. A computer-implemented system comprising a digital processing device comprising at least one processor, an operating system configured to perform executable instructions, a memory, and a computer program including instructions executable by the digital processing device to create an application of evaluating test-retest precision of a test and a retest of a plurality of subjects using fractional rank precision (FRP) or mean-average precision (MAP), comprising:

a) a software module configured to collect a test result and a retest result from each of the plurality of subjects, wherein the test result and the retest result are described in one or more feature spaces and one of the test result and the retest result is collected from a vision test machine; b) a software module configured to select a first subject from the plurality of subjects and a first test result of the first subject; c) a software module configured to calculate distances from the first test result to the retest result of each of the plurality of subjects; d) a software module configured to assess a similarity between the first test result and the retest result of each of the plurality of subjects by ranking the distances in a non-descending order; e) a software module configured to assess a rank precision for the first subject based on a rank of a distance from the first test result to the retest result of the first subject; f) a software module configured to repeat b), c), d), and e) for each of the plurality of subjects; and g) a software module configured to evaluate the test-retest precision based on the rank precision for each of the plurality of subjects.

2. The system of claim 1, wherein the test is a first vision test.

3. The system of claim 2, wherein the retest is a repeat of the first vision test after a therapy or treatment at a different time point.

4. The system of claim 2, wherein the first vision test is one or more selected from: a vision acuity test, a CSF test, and an OCT test.

5. The system of claim 1, wherein the feature space is one-dimensional or multi-dimensional.

6. The system of claim 1, wherein a feature of the feature space includes one or more features selected from: a median AULCSF computed over the spatial frequency range of 1.5 to 6 cpd, a median AULCSF computed over the spatial frequency range of 6 to 12 cpd, a median AULCSF computed over the spatial frequency range of 12 to 18 cpd, a median AULCSF computed over the spatial frequency range of 1.5 to 18 cpd, a CSF acuity, a parameter of CSF, a contrast sensitivity for at least one spatial frequency selected from 1, 1.5, 3, 6, 12, and 18 cpd, a peak sensitivity of the CSF, and a spatial frequency at which a CSF reaches a pre-determined contrast threshold.

7. The system of claim 1, wherein the rank is a real number ranging from 0 to N−1, N being a total number of subjects in the plurality of subjects.

8. The system of claim 1, wherein the distance is one or more selected from: a Euclidean distance, a Manhattan distance, and a Mahalanobis distance.

9. The system of claim 1, wherein the software module configured to assess a rank precision for the first subject is configured to:
   a) calculate a normalized rank, the normalized rank being the rank of the distance divided by a total number of subjects of the plurality of subjects; and
   b) calculate the rank precision, the rank precision being equal to one subtracted by the normalized rank.

10. The system of claim 1, wherein the rank precision is an inverse of the rank of the retest result of the first subject.

11. The system of claim 1, wherein the test-retest precision is mean of the rank precision for each of the plurality of subjects.

12. The system of claim 1, wherein the rank is a real number ranging from 1 to N, N being a total number of subjects of the plurality of subjects.

13. The system of claim 1, wherein the vision test machine is one or more selected from: a computerized adaptive contrast sensitivity testing device, a qCSF testing device, a OCT machine, a MRI machine, an ultrasound machine, a visual field testing machine, a fundus photography system, a dark adaptation measurement machine, an auto-refractor machine, a frequency-doubling threshold machine, a tonometer machine, an aberrometer machine, an eye-tracking device, and an ocular alignment machine.

* * * * *